US009028855B2

(12) United States Patent
Clement et al.

(10) Patent No.: US 9,028,855 B2
(45) Date of Patent: May 12, 2015

(54) PLANT ADDITIVES AND USES THEREOF TO MODULATE THE SYNTHESIS OF MEMBRANE GLYCEROLIPIDS IN PLANTA

(75) Inventors: Mathilde Clement, Vallauris (FR); Thierry Desnos, Pertruis (FR); Laurent Nussaume, La Tour d'Aigues (FR)

(73) Assignee: Commissariat a l'Energie Atomique et aux Energies Alternatives, Paris (FR)

( * ) Notice: Subject to any disclaimer, the term of this patent is extended or adjusted under 35 U.S.C. 154(b) by 228 days.

(21) Appl. No.: 13/496,771

(22) PCT Filed: Sep. 17, 2010

(86) PCT No.: PCT/IB2010/002571

§ 371 (c)(1),
(2), (4) Date: May 29, 2012

(87) PCT Pub. No.: WO2011/033389

PCT Pub. Date: Mar. 24, 2011

(65) Prior Publication Data

US 2012/0283101 A1 Nov. 8, 2012

(30) Foreign Application Priority Data

Sep. 17, 2009 (EP) .................................... 09290709

(51) Int. Cl.

| | |
|---|---|
| ***A01N 37/44*** | (2006.01) |
| ***A01N 35/06*** | (2006.01) |
| ***A01N 35/08*** | (2006.01) |
| ***A01N 35/10*** | (2006.01) |
| ***A01N 41/10*** | (2006.01) |
| ***A01N 43/30*** | (2006.01) |
| ***A01N 43/40*** | (2006.01) |
| ***A01N 43/54*** | (2006.01) |

(52) U.S. Cl.

CPC ................ *A01N 37/44* (2013.01); *A01N 35/06* (2013.01); *A01N 35/08* (2013.01); *A01N 35/10* (2013.01); *A01N 41/10* (2013.01); *A01N 43/30* (2013.01); *A01N 43/40* (2013.01); *A01N 43/54* (2013.01); *Y02E 50/10* (2013.01)

(58) Field of Classification Search

None

See application file for complete search history.

(56) References Cited

FOREIGN PATENT DOCUMENTS

JP 06-256273 9/1994

OTHER PUBLICATIONS

Wang, Photobleaching Activity of 2-(Phenylamino)methylidenecyclohexane-1,3-diones in Tobacco (*Nicotiana tabacum*) Cultured Cells, Journal of Agricultural and Food Chemistry, 45, pp. 2728-2734, 1997.

Zacharias Uber Anilinomethylenverbindungen der Cyclohexandione Monatschefte Fur Chemie, 105, pp. 1283-1291, 1974.

Wolfbeis, The Reactivity of C=N-Double Bond Systems, X1 Synthesis of Condensed Heterocycles, Zeitschrift Fuer Naturforschung, 31, pp. 1519-1525, 1976.

*Primary Examiner* — Bethany Barham
*Assistant Examiner* — Barbara Frazier
(74) *Attorney, Agent, or Firm* — Morgan, Lewis & Bockius LLP

(57) ABSTRACT

The present invention pertains to plant additives containing a molecule selected in a family of compounds, wherein said molecule can modulate some molecular markers and physiological modifications observed in cases of phosphate deficiency.

Figure 1:
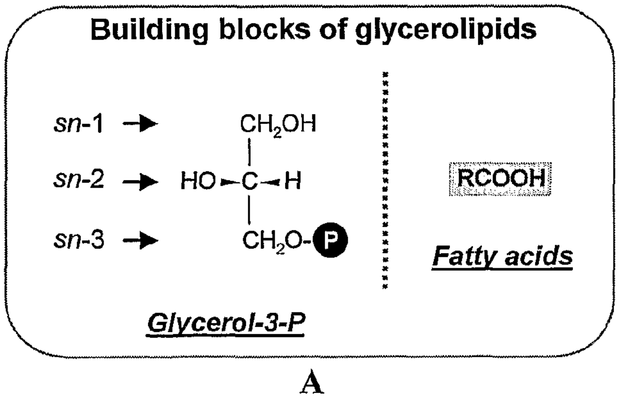
Figure 1:
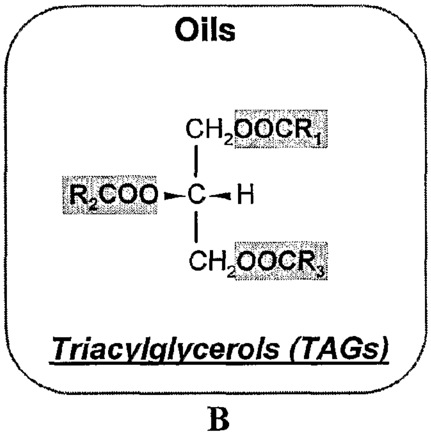
Figure 1:
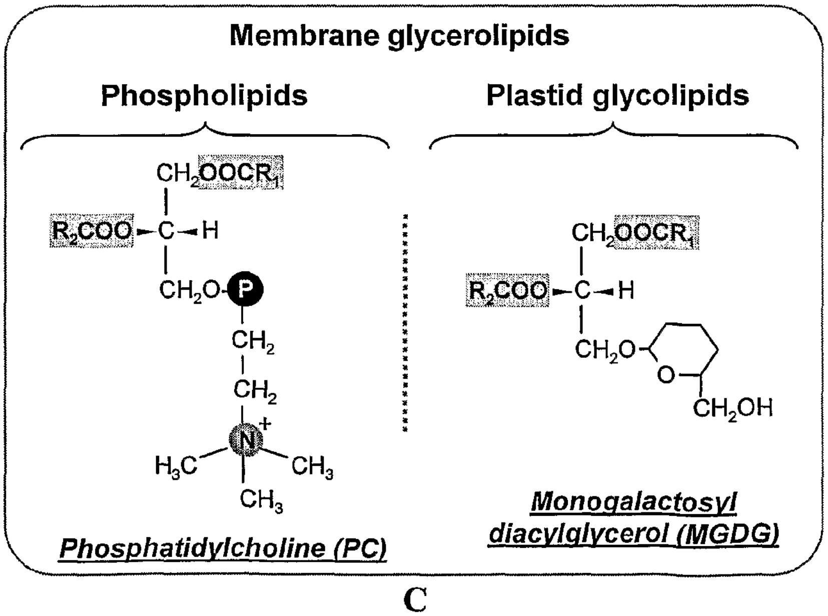

The family of compounds comprises the molecule MC2 of formula

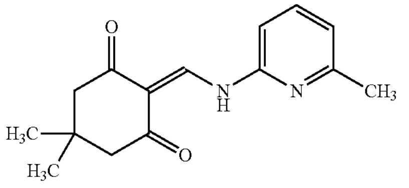

as well as analogs thereof.

7 Claims, 11 Drawing Sheets

A

B

C

PLANT ADDITIVES AND USES THEREOF TO MODULATE THE SYNTHESIS OF MEMBRANE GLYCEROLIPIDS IN PLANTA

RELATED APPLICATIONS

The present application is a U.S. National Phase Application of International Application No. PCT/IB2010/002571 (filed Sep. 17, 2010) which claims priority to European Application No. 09290709.6 (filed Sep. 17, 2009) which are hereby incorporated by reference in their entirety.

Phosphate (P) is an essential macronutrient required for plant growth and development. Often present in limited amounts in soils, phosphate is trapped in organic or mineral forms, and this fixation results in its low availability for plants.

In order to increase the productivity of crops, the low inorganic phosphate (Pi) content of agricultural soils is supplemented by the application of large quantities of phosphate fertilizers. However, most of these applied inputs remain unavailable for the plants due to organic fixation and inorganic complexation, and the wide use of these fertilizers raises environmental concerns. Indeed, phosphate minerals often contain trace amounts of dangerous substances such as arsenic, cadmium, polonium and uranium, and if no cleaning step is applied after mining, the continuous use of phosphate fertilizers can lead to an accumulation of these elements in the soil. Moreover, due to an increased demand, the price of phosphate has drastically increased since 2007. Therefore, there is a need of non-phosphate plant additives which can help phosphate uptake by the plants, in order to reduce phosphate inputs without decreasing the plants growth.

In cases of phosphate deficiency, plants exhibit drastic changes which increase P acquisition from soils and improve its use in the plant. Pi starvation leads to morphological modifications such as significant growth reduction, anthocyanin accumulation in the leaves and a modified root architecture to explore P-richer horizons. Phosphate starvation also induces numerous biochemical changes (Raghothama, 1999). Phosphate uptake is enhanced by a combination of an increased number of phosphate transporters, in particular Pht1;4 (Misson et al., 2004), and the secretion of organic acids and enzymes such as phosphatases and nucleases into the rhizosphere. Using *Arabidopsis thaliana* whole genome Affymetrix gene chip (ATH1), Misson et al. have studied the global gene expression in response to Pi deprivation to quantify the spatio-temporal variations in transcript abundance of 22,810 genes (Misson et al., 2005). The analysis revealed a coordinated induction and suppression of 612 and 254 Pi-responsive genes, respectively. The functional classification of some of these genes indicated their involvement in various metabolic pathways, ion transport, signal transduction, transcriptional regulation, and other processes related to growth and development. In particular, this study demonstrated that several metal transporters were induced in phosphate-deprived plants, and that a significant amount of responsive genes are involved in lipid biosynthetic pathways (Misson et al., 2005).

There are 3 main lipid classes in plant biomass: 1) triacylglycerols (or oils), 2) phosphorus-containing glycerolipids (or phospholipids) and 3) phosphorus-free sulfo and galactolipids (plastid glycolipids). Most abundant lipids provided by plants for nutritional or non-nutritional purposes are detailed below:

Glycerolipids

Their molecular structure is a 3-carbone glycerol backbone esterified by one, two or three fatty acids (FIG. 1A). Main glycerolipids in plant biomass are triacylglycerols (or oils), phosphorus-containing glycerolipids (or phospholipids) and phosphorus-free sulfo and galactolipids (plastid glycolipids).

Glycerolipids with three acyls, or triacylglycerols (TAGs), are a major form of storage of carbon and energy within cells, and are known as oils (FIG. 1B). Oilseed crops are the primary source of nutritional oils. In the gut, their hydrolysis releases essential fatty acids, which cannot be synthesized by human cells. Plant oil is healthier than animal fat, and recommended against overweight and heart diseases. Efforts have focused on the engineering of fatty acid synthesis, to increase the proportion of acyls of therapeutic interest. Increasing TAG in seeds is also an important but difficult issue, and production of TAG in non-seed organs is now envisaged to face additional demand (Durrett et al., 2008).

Oil can also be converted into gasoline, called biofuel or biodiesel. This utilization is debated since the current production of vegetable oils would only cover a fraction of gasoline demand, and divert oilseed production from nutrition. Efforts are therefore put to produce oil in other organs of plants, such as leaves (Durrett et al., 2008) or in other organisms like algae (Chisti, 2007). By contrast with seeds, production of oils in leaves should cope with the presence of large amounts of membrane glycerolipids including phospholipids and plastid glycolipids (FIG. 1C).

Glycerolipids with two acyls make the bulk of biological membrane. The non-acylated carbon of the glycerol backbone can harbour a polar head determining its orientation within the membrane bilayers and its biological function. This polar head can be phosphated, in phospholipids, which is the most abundant membrane lipid in animal cells, and in plant cells outside plastids. The polar head can also be devoid of phosphate, like in glycolipids abundantly synthesized within chloroplast membranes, and uniquely found in plastid-containing organisms.

Phospholipids

Phospholipids contain up to one third of the phosphate content in plants, and are a primary source of P in human nutrition in lecithin mixtures. Most abundant phospholipids are phosphatidylcholine (PC) and phosphatidylethanolamine (PE). Commercial soybean lecithin mixtures contain ~70% phospholipids together with TAGs. Edible phospholipids are recommended for human health, and increasing phospholipid proportion in that context would be interesting. Vice versa, phospholipids are also considered detrimental for both edible oils and for conversion of oil into biodiesel. In this latter case, phospholipid impurities cause clogging deposits in engines, and are a limitation for use of crude oils as gasoline substitutes. Numerous research projects focus therefore on their removal, called "oil degumming", by filtration/decantation or lipase treatments. High phospholipid level in leaves is therefore a limitation for any project aiming at producing oils in these organs for biodiesel applications. Thus, high or low phospholipid concentrations in plant tissues have their interest. In conditions like under low-Pi supply, phospholipids are converted into PC, which is then converted into plastid glycolipids.

Plastid Glycolipids

Plastid glycolipids consist of mono- and digalactolipids (MGDG, DGDG), and the quantitatively minor sulfoquinovosyldiacylglycerol (SQDG), often called sulfolipid. Galactolipids are the major glycerolipid in chloroplast membranes, and therefore the most abundant lipid in green tissues. Galactolipids are important for the quality of flour in the bread-baking process (Selmair and Koehler, 2008). After ingestion, they are hydrolyzed by a pancreatic galactolipase and rapidly digested. Recent studies have demonstrated that glycolipids had also therapeutic properties: MGDG was shown to have in vivo anti-inflammatory action (Bruno et al., 2005), and anti-cancer properties, like apoptotic-inducing activities (Andrianasolo et al., 2008) and, together with DGDG and SQDG, to directly act on mammal and human effectors of cancer cell proliferation (DNA polymerase, Cdt1, p53) (Maeda et al., 2007). In addition, plastid glycolipid liposomes were shown to allow the delivery of anticancer molecules (Liguori et al., 2008). Non-nutritional use of plastid glycolipids could therefore diversify the applications of agricultural lipids.

In nature, the ratio of phospholipid vs. plastid glycolipid is finely controlled, and adjusted by plants in function of soil phosphorus availability. In low Pi supply, phospholipids are hydrolyzed, plastid glycolipid synthesis is enhanced and digalactolipid is exported outside plastids to phospholipid-impoverished membranes (Jouhet et al., 2007). In non-limiting conditions, the phospholipid/glycolipid ratio is around 50:50 in *Arabidopsis* leaves. Low phosphate availability triggers the hydrolysis of phospholipids and the accumulation of sulfo/galactolipids, leading to a phospholipid/glycolipid ratio around 20:80. This phenomenon is observed in all major crops: it was recently reported that in oat roots the DGDG/PC ratio increases by a factor of 10, from 0.25 in non-limiting Pi to ~3.0 in low-Pi supply (Tjellstrom et al., 2008).

It would be interesting to be able to reprogram the glycerolipid metabolism in a similar manner, promoting the net conversion of phospholipids into glycolipids. Decreasing the phospholipid proportion would for example be beneficial since they are detrimental in oils. In addition, the phospholipids which are considered as a waste in this context, would be converted in planta into glycolipids with added value. Indeed, these lipids are essential for photosynthesis and the quality of some processed food, and they could be extracted and purified for biomedical purposes. However, the net conversion of phospholipids into glycolipids by mimicking the response of plants to low phosphate supply, but without impacting on the biomass, appears as a technological barrier.

Hence, there is currently a need for molecules which can act on the glycerolipid remodelling mechanisms to modulate the membrane glycerolipids synthesis in planta.

By using a chemogenetic screening approach (targeting the phosphate transporter Pht1;4), the inventors have identified a molecule, called MC2, which modulates several molecular markers of phosphate deficiency (induction of Pht1;4, Pldz2, mgd3 and inhibition of Ira), as well as the majority of physiological modifications observed in cases of phosphate deficiency (starch and anthocyanins accumulation, inhibition of the growth of the primary root, modification of the glycolipids composition, induction of phosphatases, . . . ).

Then, by screening a large number of MC2 analogs, they identified a family of compounds which can selectively act on some of these markers and associated modifications. These results are summarized in Table 1 of the experimental part below. These surprising results pave the way to novel agricultural and bio-industrial practices based on the tuning of membrane glycerolipids synthesis in planta. Depending on several factors detailed below, the present invention enables a reduction of the need for phosphate input in soils, and/or a combination of high yields (obtained in presence of abundant phosphate) and production of interesting glycolipids usually reduced by such agricultural practice.

Thus, advantageously, it has been demonstrated that this family of compounds, when used in a plant additive, is able to redirect the metabolism of the plant toward that of a plant having a phosphate deficiency and hence to modify the profile, notably the relative ratio, of the energy storage molecules, such as starch, phospholipids and glycolipids.

A first aspect of the present invention is a plant additive comprising a compound of formula 1:

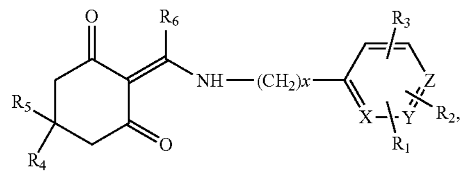

(1)

wherein x is an integer selected amongst 0 and 1;

X, Y, Z are selected amongst C and N and at most one of X, Y and Z is N;

$R_1$, $R_2$, $R_3$, are selected in the group of: H; a $C_1$-$C_6$ alkyl possibly substituted by one or several groups selected amongst: OR, NRR', CONRR', NO, COOR, $SO_2$, $SO_2R$, COR, $NO_2$ and a halogen; a $C_1$-$C_6$ alkenyl possibly substituted by one or several groups selected amongst: OR, NRR', CONRR', NO, COOR, $SO_2$, $SO_2R$, COR, $NO_2$ and a halogen; OR; NRR'; NO; CONRR'; COOR; $SO_2$; $SO_2R$; SR; COR; $NO_2$; and a halogen; wherein R and R', independently from each other, are selected amongst: H, a $C_1$-$C_6$ alkyl and a $C_1$-$C_6$ alkenyl;

$R_1$, $R_2$, $R_3$ are positioned on any of the carbon atoms of the aromatic cycle, wherein two neighboring groups selected amongst $R_1$, $R_2$ and $R_3$ can form a cycle or a heterocycle together;

$R_4$, $R_5$, independently from each other, are selected in the group of: H; a $C_1$-$C_6$ alkyl; a $C_1$-$C_6$ acyl and an aromatic ring; and $R_6$ is H, SH, $SCH_3$ or a $C_1$-$C_6$ alkyl.

Preferably, the plant additive comprises a compound of formula (I) wherein only one of X, Y, Z is N, the two others being C, or a compound selected from MC2 analogues #2-3, #5-10, #12, #14, #21-22, #24-27, #29-32, #34-45, and #47.

More specifically, the invention pertains to a plant additive comprising a compound of formula 1, wherein x=0;

X, Y, Z are selected amongst C and N and at most one of X, Y and Z is N;

$R_1$, $R_2$, $R_3$, independently from each other, are selected in the group of: H; a $C_1$-$C_6$ alkyl possibly substituted by one or several groups selected amongst: OH, OR, $NH_2$, NHR, $CONH_2$, NO, CONHR, COOH, COOR, $SO_2$, $SO_2R$, COH, COR, $NO_2$ and a halogen; a $C_1$-$C_6$ alkenyl possibly substituted by one or several groups selected amongst: OH, OR, $NH_2$, NHR, $CONH_2$, NO, CONHR, COOH, COOR, $SO_2$, SOR, COH, COR, $NO_2$ and a halogen; OH; OR; $NH_2$; NO; NHR; $CONH_2$; CONHR; COOH; COOR; $SO_2$; $SO_2R$; $SCH_3$; COH; COR; $NO_2$; and a halogen, wherein R is a $C_1$-$C_6$ alkyl or a $C_1$-$C_6$ alkenyl;

$R_1$, $R_2$, $R_3$ are positioned on any of the carbon atoms of the aromatic cycle, wherein two neighboring groups selected amongst $R_1$, $R_2$ and $R_3$ can form a cycle or a heterocycle together;

$R_4$, $R_5$, independently from each other, are selected in the group of: H; a $C_1$-$C_6$ alkyl; a $C_1$-$C_6$ acyl; a benzene; and $R_6$ is H.

By "plant additive" is herein meant any kind of soil additive, soil amendment, fertilizer or soil conditioner, which can of course be used to modify a soil, but also in hydroponic cultures. Preferably, the plant additive is non herbicidal.

Examples of compounds which can be used in plant additives according to the invention are disclosed in the following table:

TABLE 1

| MC2 and examples of MC2 analogues which can be used in plant additives according to the invention | |
|---|---|
| Name | Formula |
| MC2 | 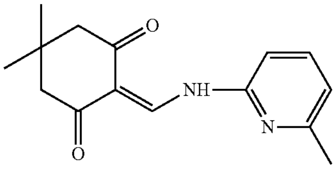 |
| #1 | 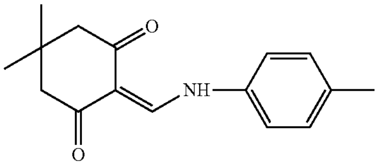 |
| #2 | 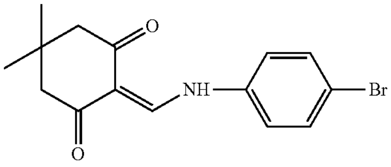 |
| #3 | 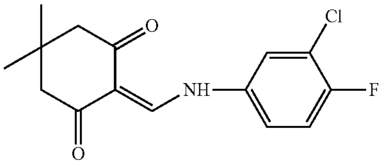 [SMILES: CC1(C)CC(=O)C(=CNc2ccc(F)c(Cl)c2)C(=O)C1] |
| #4 | 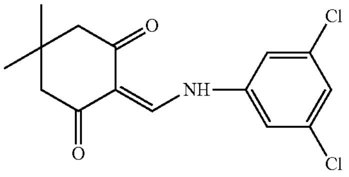 [SMILES: CC1(C)CC(=O)C(=CNc2cc(Cl)cc(Cl)c2)C(=O)C1] |
| #5 | 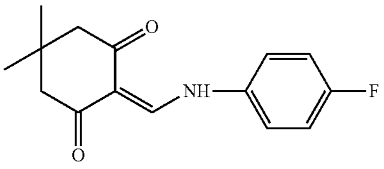 |
| #6 | 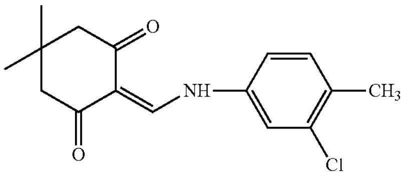 |

TABLE 1-continued

| MC2 and examples of MC2 analogues which can be used in plant additives according to the invention | |
|---|---|
| Name | Formula |
| #7 | 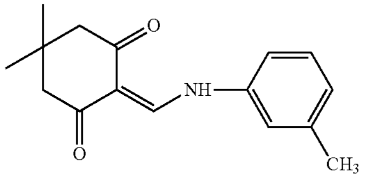 |
| #8 | 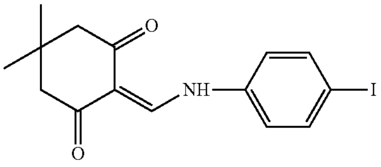 [SMILES: CC1(C)CC(=O)C(=CNc2ccc(I)cc2)C(=O)C1] |
| #9 | 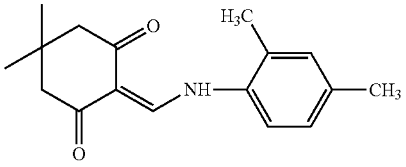 |
| #10 | 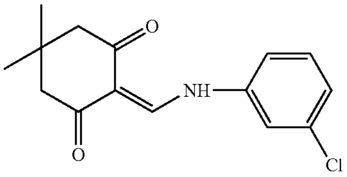 [SMILES: CC1(C)CC(=O)C(=CNc2cccc(Cl)c2)C(=O)C1] |
| #11 | 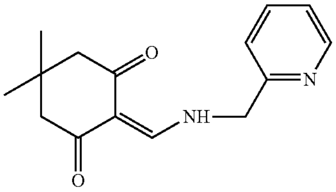 [SMILES: CC1(C)CC(=O)C(=CNCc2ccccn2)C(=O)C1] |
| #12 | 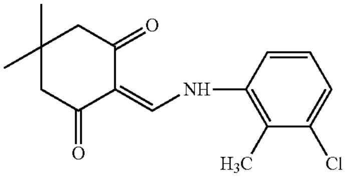 [SMILES: Cc1c(Cl)cccc1NC=C1C(=O)CC(C)(C)CC1=O] |
| #13 | 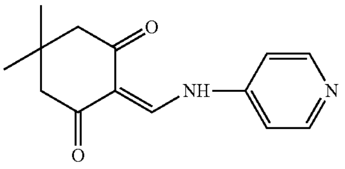 [SMILES: CC1(C)CC(=O)C(=CNc2ccncc2)C(=O)C1] |
| #14 | 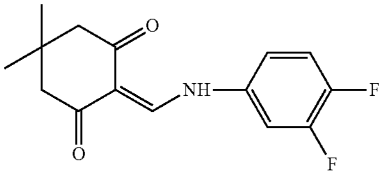 [SMILES: CC1(C)CC(=O)C(=CNc2ccc(F)c(F)c2)C(=O)C1] |

TABLE 1-continued
| MC2 and examples of MC2 analogues which can be used in plant additives according to the invention | |
|---|---|
| Name | Formula |
| #15 | 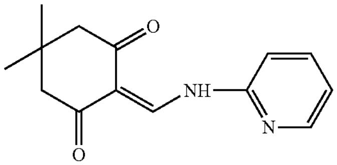 [SMILES: CC1(C)CC(=O)C(=CNc2ccccn2)C(=O)C1] |
| #16 | 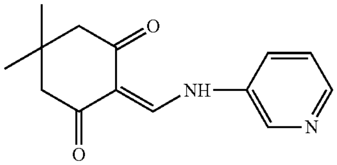 |
| #17 | 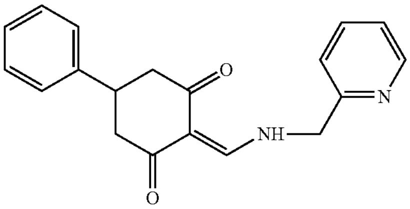 [SMILES: O=C1CC(c2ccccc2)CC(=O)C1=CNCc1ccccn1] |
| #19 | 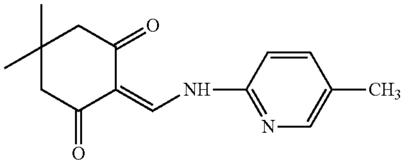 |
| #20 | 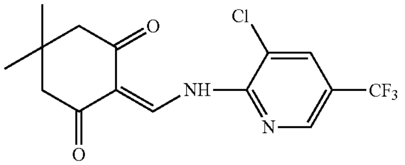 [SMILES: CC1(C)CC(=O)C(=CNc2ncc(C(F)(F)F)cc2Cl)C(=O)C1] |
| #22 | 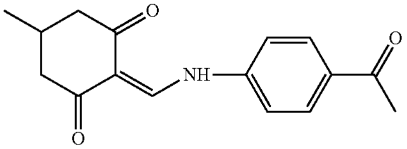 [SMILES: CC(=O)c1ccc(NC=C2C(=O)CC(C)CC2=O)cc1] |
| #23 | 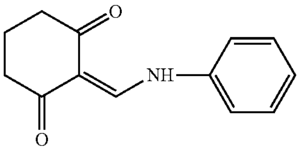 [SMILES: O=C1CCCC(=O)C1=CNc1ccccc1] |
| #24 | 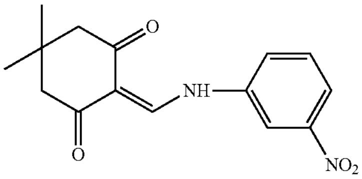 |
TABLE 1-continued
| MC2 and examples of MC2 analogues which can be used in plant additives according to the invention | |
|---|---|
| Name | Formula |
| #25 | 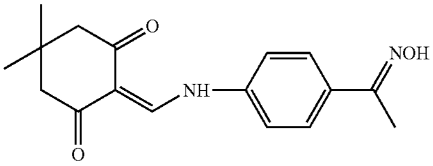 |
| #27 | 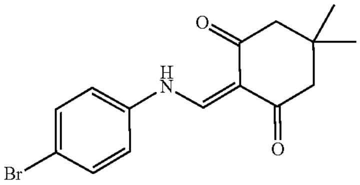 |
| 28 | 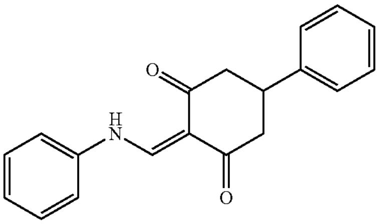 [SMILES: O=C1CC(c2ccccc2)CC(=O)C1=CNc1ccccc1] |
| 29 | 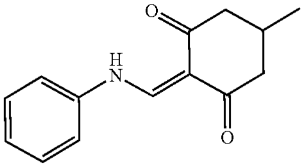 |
| 30 | 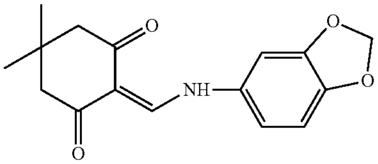 [SMILES: CC1(C)CC(=O)C(=CNc2ccc3c(c2)OCO3)C(=O)C1] |
| 31 | 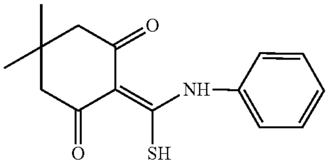 [SMILES: CC1(C)CC(=O)C(=C(S)Nc2ccccc2)C(=O)C1] |
| #32 | 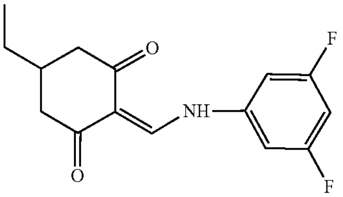 [SMILES: CCC1CC(=O)C(=CNc2cc(F)cc(F)c2)C(=O)C1] |
| #33 | 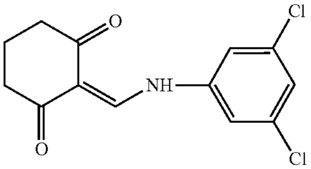 [SMILES: O=C1CCCC(=O)C1=CNc1cc(Cl)cc(Cl)c1] |

TABLE 1-continued

MC2 and examples of MC2 analogues which can be used in plant additives according to the invention

| Name | Formula |
|---|---|
| #34 | 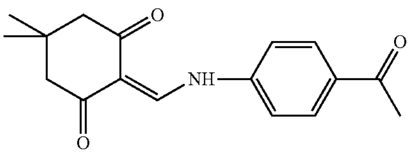 [SMILES: CC(=O)c1ccc(NC=C2C(=O)CC(C)(C)CC2=O)cc1] |
| #35 | 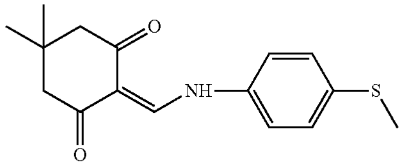 |
| #36 | 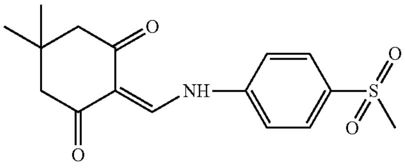 [SMILES: CC1(C)CC(=O)C(=CNc2ccc(S(C)(=O)=O)cc2)C(=O)C1] |
| #37 | 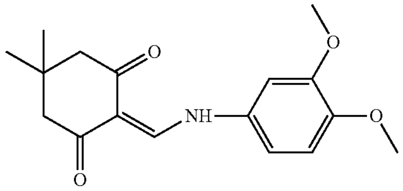 |
| #38 | 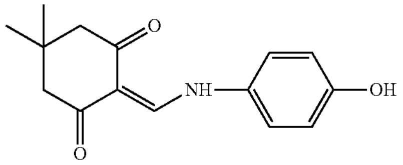 [SMILES: CC1(C)CC(=O)C(=CNc2ccc(O)cc2)C(=O)C1] |
| #39 | 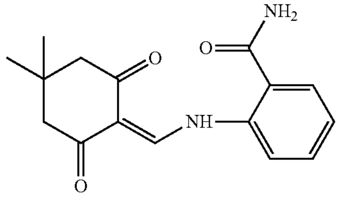 [SMILES: CC1(C)CC(=O)C(=CNc2ccccc2C(N)=O)C(=O)C1] |
| #40 | 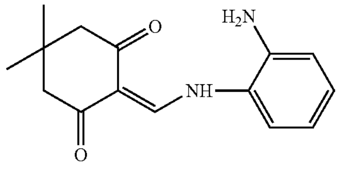 [SMILES: CC1(C)CC(=O)C(=CNc2ccccc2N)C(=O)C1] |
| #41 | 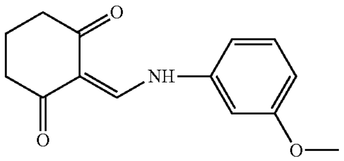 [SMILES: COc1cccc(NC=C2C(=O)CCCC2=O)c1] |
| #42 | 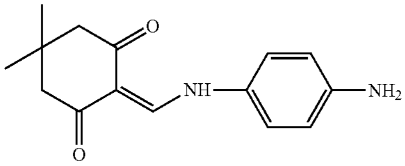 [SMILES: CC1(C)CC(=O)C(=CNc2ccc(N)cc2)C(=O)C1] |
| #43 | 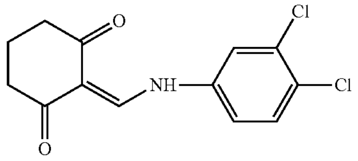 [SMILES: O=C1CCCC(=O)C1=CNc1ccc(Cl)c(Cl)c1] |
| #44 | 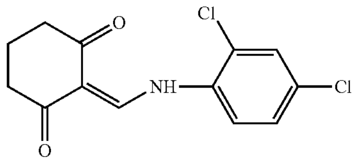 [SMILES: O=C1CCCC(=O)C1=CNc1ccc(Cl)cc1Cl] |
| #45 | 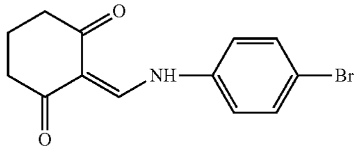 [SMILES: O=C1CCCC(=O)C1=CNc1ccc(Br)cc1] |
| #46 | 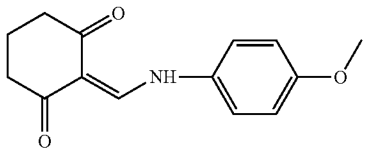 [SMILES: COc1ccc(NC=C2C(=O)CCCC2=O)cc1] |
| #47 | 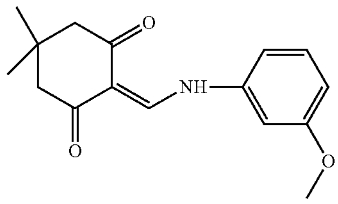 [SMILES: COc1cccc(NC=C2C(=O)CC(C)(C)CC2=O)c1] |

In one preferred embodiment, the compound of formula 1 induces an up-regulation of the Pht1;4 gene in plants when added to the cultivation medium. Non-limitative examples of compounds which can be used according to this embodiment are MC2 and its analogues #1-7, 9-16, 19-20, 22, 24-25, 27-28, 32-34, 36-39, 43-44, and 47 described in Table 1 above. This functional property, as well as the other properties mentioned below, can be tested by using the protocols and the materials described in the experimental part which follows. Depending on the application, the skilled artisan will test these properties in roots, in seeds, in leaves or in several of these elements (or in a mixture of several parts of the plant). A preferred plant additive according to the present invention hence comprises at least one compound selected in the group consisting of MC2 and its analogues #1-7, 9-16, 19-20, 22, 24-25, 27-28, 32-34, 36-39, 43-44 and 47, or a combination thereof.

According to another preferred embodiment, the compound of formula 1, when added to the cultivation medium of plants, induces in said plants an up-regulation of one or both of the genes encoding the phospholipase DZ2 and the MGD3 enzyme. All the compounds which have been tested and which are described in Table 1, except MC2 analogue #8, have this property, at least in leaves. Preferred plant additives according to this embodiment comprise at least one compound selected in the group consisting of MC2 and its analogues #1-8, #9-17, #19-20, #22-25, #27-47, or a combination thereof. They are particularly useful for growing plants for biofuel (also called biodiesel) production.

A plant additive comprising a compound inducing a change in the lipids pattern, especially a decrease of the phospholipid/glycolipid ratio, without significantly impacting on plant growth nor on the expression of the phosphate transporter PHT1;4, can advantageously be used for growing plants for the production of biodiesel, and/or for the production of plastid glycolipids. Non-limitative examples of compounds which can advantageously be used for this application due to their specificity in lipids remodeling, are the analogues of MC2 which are referenced in Table 1 as #23, #29, #30, #31, #40, #41, #42, #45 and #46, as well as combinations thereof.

Compounds such as #27 or #28 (and, to a lesser extent, MC2 and its analogues #5, #20, #22, #37, #43, #44 and #47), which do not induce a reduction of the root growth, despite the fact that they induce expression of the Pht1;4 gene, can also be used for the above applications. Another advantageous application of a compound having such properties is its use in a soil additive for decreasing the need of phosphate-containing fertilizers. Indeed, the addition of such a compound (or of a mixture of such compounds) to a plant medium/soil will increase the capacity of said plant to mobilize and/or uptake the inorganic phosphate which is present in said medium or soil. Since these compounds do not per se limit the plant growth, they will, to the contrary, favour the growth in a phosphate-poor environment.

According to another embodiment, the plant additive according to the invention comprises a compound of formula 1 which induces an up-regulation of the iron transporter IRT1 in plants, when added to the cultivation medium. Examples of such compounds tested by the inventors are MC2 analogues referred to as #1-3, #5, #7-15, #19-20, #22-25, and #27-47. Plant additives comprising these compounds can advantageously be used for increasing phytoremediation of heavy metals, since an increase of iron uptake is usually associated to an increase of uptake of all metals.

In another aspect, the invention relates to the use of a plant additive for growing plants either for biofuel production or for plastid glycolipids production, or for reducing the need for phosphate fertilizer for growing plants, said plant additive comprising a compound of formula 1:

(1)

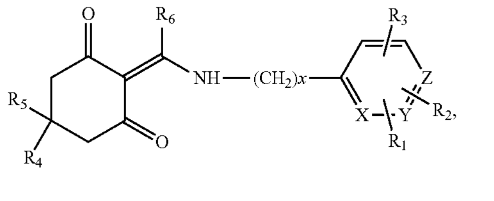

wherein x is an integer selected amongst 0 and 1;

X, Y, Z are selected amongst C and N an at most one of X, Y and Z is N;

$R_1$, $R_2$, $R_3$, are selected in the group of: H; a $C_1$-$C_6$ alkyl possibly substituted by one or several groups selected amongst: OR, NRR', CONRR', NO, COOR, $SO_2$, $SO_2R$, COR, $NO_2$ and a halogen; a $C_1$-$C_6$ alkenyl possibly substituted by one or several groups selected amongst: OR, NRR', CONRR', NO, COOR, $SO_2$, $SO_2R$, COR, $NO_2$ and a halogen; OR; NRR'; NO; CONRR'; COOR; $SO_2$; $SO_2R$; SR; COR; $NO_2$; and a halogen; and R and R' independently from each other, are selected amongst: H, a $C_1$-$C_6$ alkyl and a $C_1$-$C_6$ alkenyl;

$R_1$, $R_2$, $R_3$ are positioned on any of the carbon atoms of the aromatic cycle, wherein two neighboring groups selected amongst $R_1$, $R_2$ and $R_3$ can form a cycle or a heterocycle together;

$R_4$, $R_5$, independently from each other, are selected in the group of: H; a $C_1$-$C_6$ alkyl; a $C_1$-$C_6$ acyl and an aromatic ring; and $R_6$ is H, SH, $SCH_3$ or a $C_1$-$C_6$ alkyl.

In one embodiment, the plant additive is used for growing plants for biofuel production, or for plastid glycolipids production.

Preferably, the biofuel is bioethanol.

In another embodiment, the plant additive is used for reducing the need for phosphate fertilizer for growing plants.

Other characteristics of the invention will also become apparent in the course of the description which follows of the experimental data obtained by the inventors and which provide it with the required experimental support, without limiting its scope.

LEGENDS TO THE FIGURES

FIG. 1: Structure of the three main lipid classes in plants. A. Glycerolipids. B. Triacylglycerols. C. Membrane glycerolipids.

Figure 2:
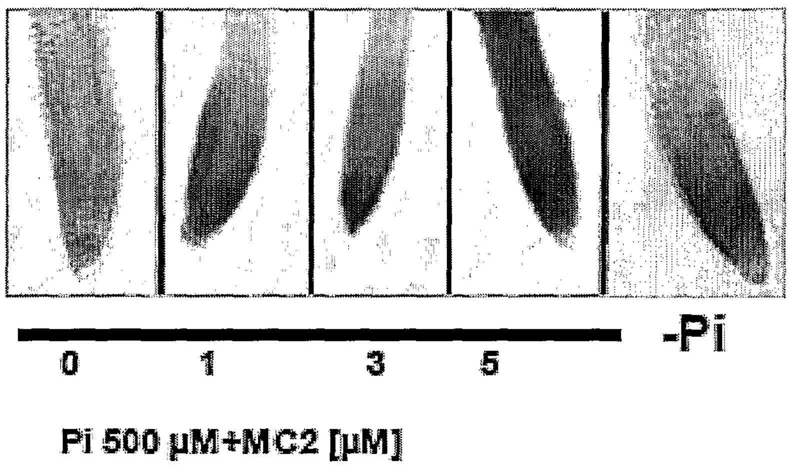

FIG. 2: Histochemical localisation of the GUS activity in root tip of pht1;4-1 grown in high phosphate medium (500 μM) supplied with MC2 or grown in low phosphate medium.

Figure 3:
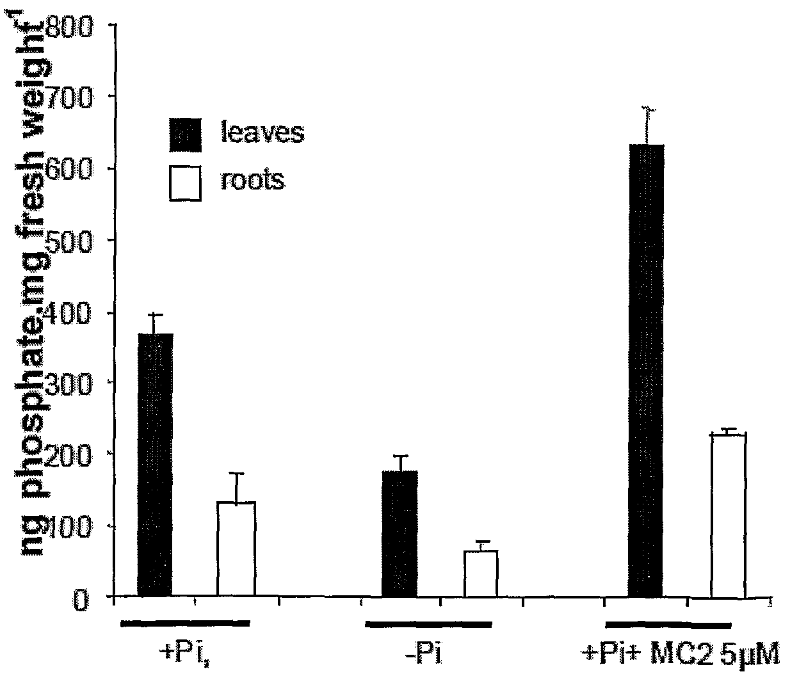

FIG. 3: Pi content measurements in leaves and in roots of ten day-old wild-type seedlings grown in high phosphate, in low phosphate medium, and in high phosphate medium supplied with 50 μM of MC2. Values represent the mean of 3 experiment±SD.

Figure 4:
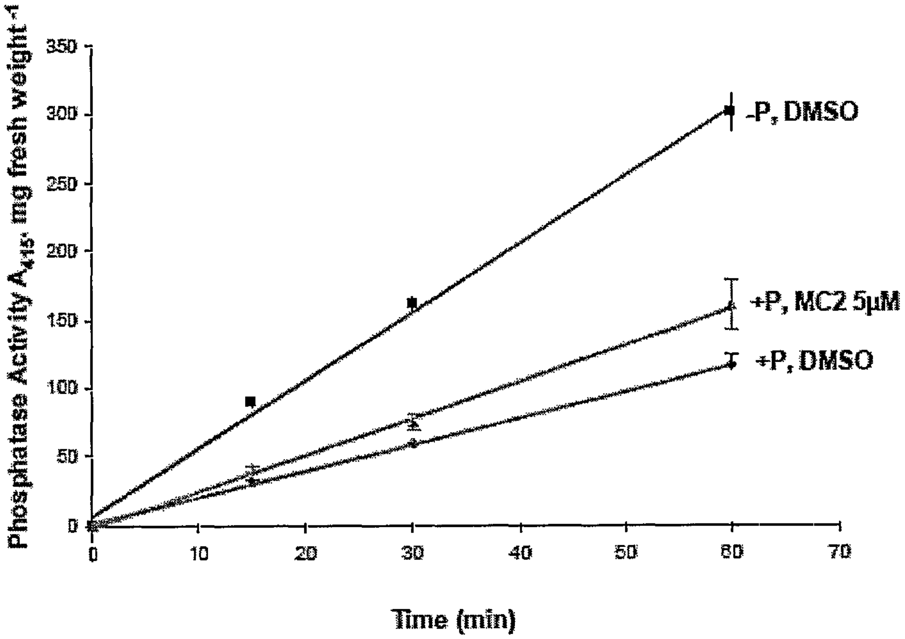

FIG. 4: Acid phosphatase activity was assayed spectrophotometrically in root extract from 10 days old plants grown in high phosphate medium, in low phosphate medium or in high phosphate medium supplied with 5 μM of MC2. Values represent the mean of 3 experiments±SD.

Figure 5:
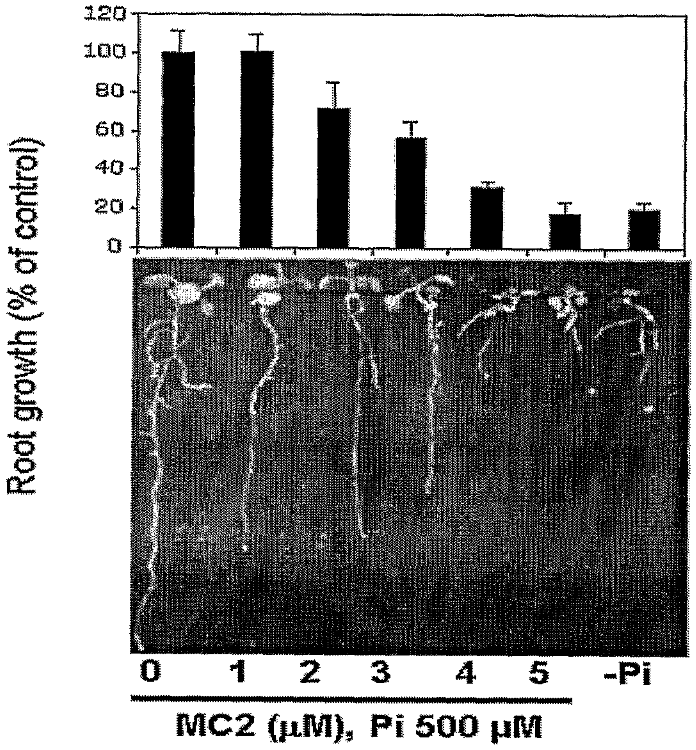

FIG. 5: Root growth analysis in response to high phosphate medium, low phosphate medium or high phosphate medium supplied with MC2. Values are expressed in % of control and represent the mean of 12 plants±SD.

Figure 6:
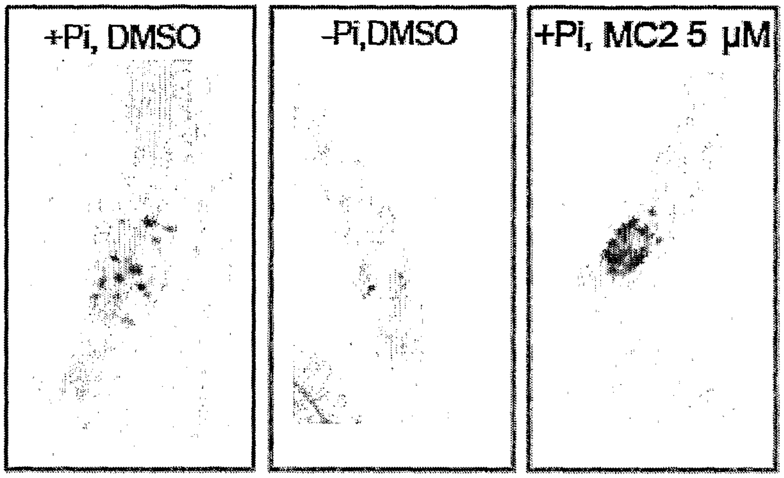

FIG. 6: Histochemical localisation of the GUS activity in root tip of Cyclin B1 grown in high phosphate medium (500 μM) supplied with MC2 (5 μM) or grown in low phosphate medium.

Figure 7:
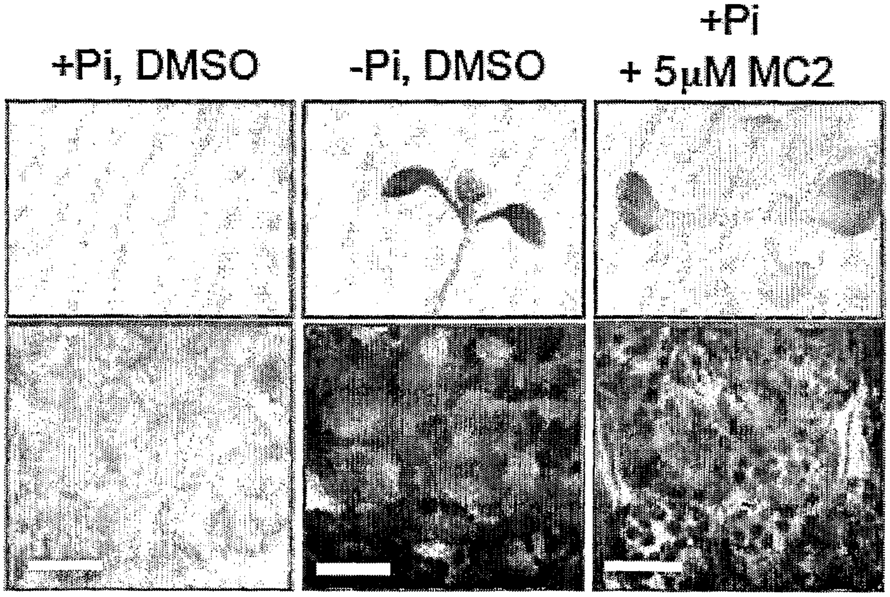

FIG. 7: Starch contents of 10 days old wild type seedlings. Plants were grown on high phosphate medium, low phosphate medium, or high phosphate medium supplied with MC2 (5 μM). Starch was made visible by iodine staining.

Figure 8:
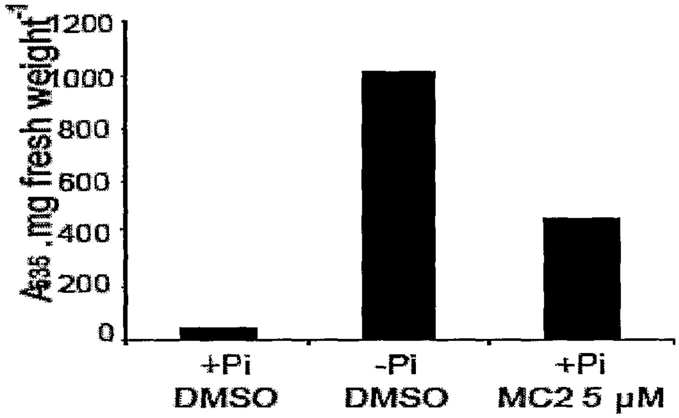

FIG. 8: Anthocyanins contents of 10 days old wild type seedlings. Plants were grown on high phosphate medium, low phosphate medium, or high phosphate medium supplied with MC2 (5 μM). Anthocyanins levels were determined spectrophotometrically.

Figure 9:
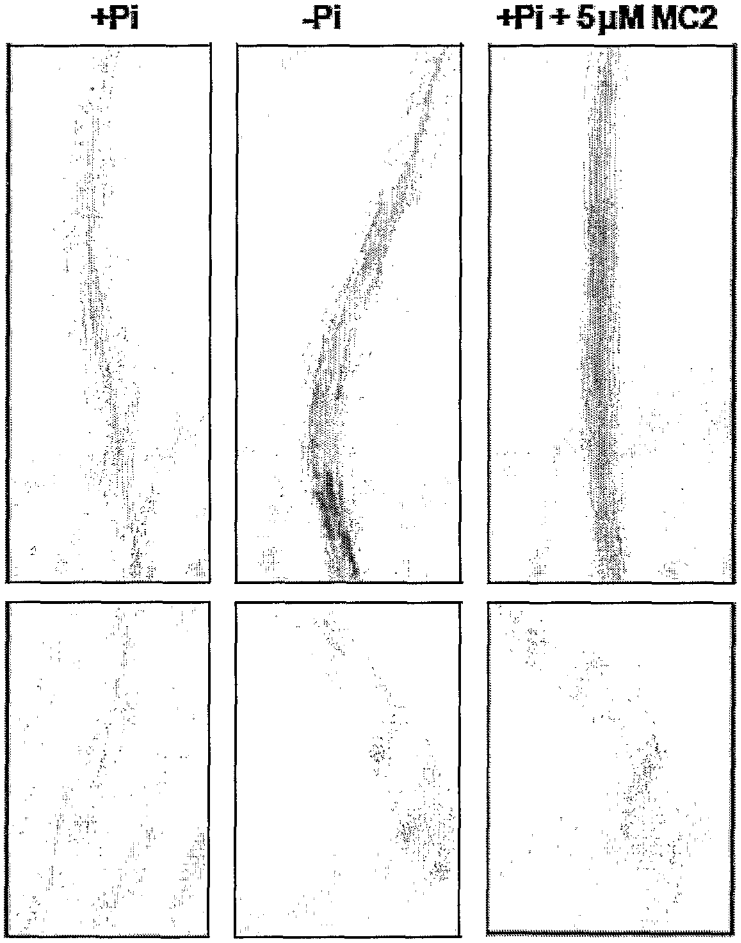

FIG. 9: Histochemical localisation of the GUS activity in root tip of MGD3 grown in high phosphate medium (500 μM) supplied with MC2 (5 μM) or grown in low phosphate medium.

Figure 10:
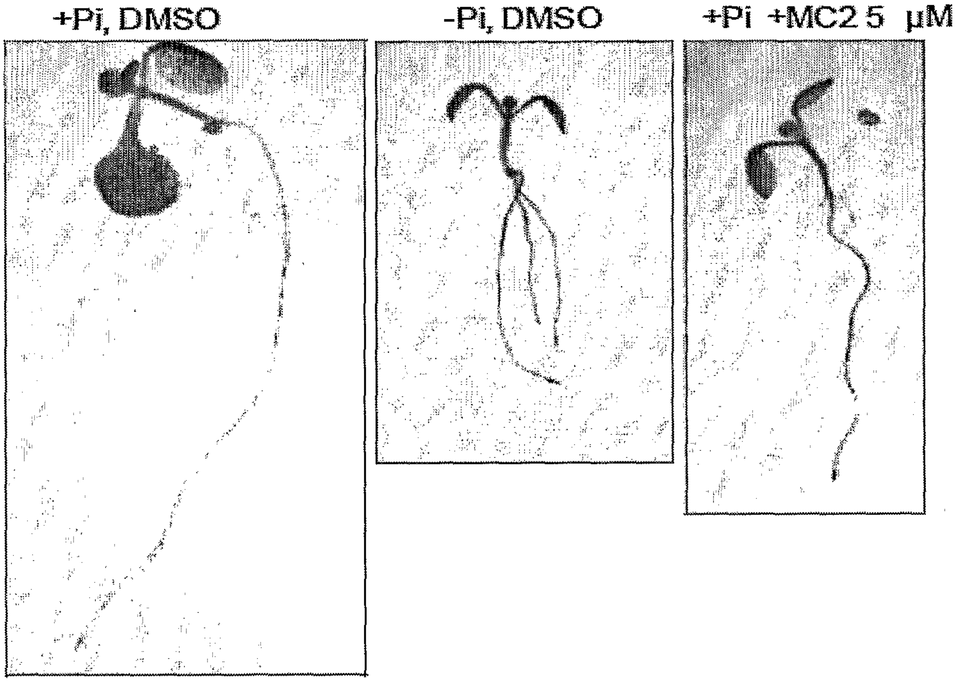

FIG. 10: Histochemical localisation of the GUS activity in root tip of PLDζ2 grown in high phosphate medium (500 μM) supplied with MC2 (5 μM) or grown in low phosphate medium.

Figure 11:
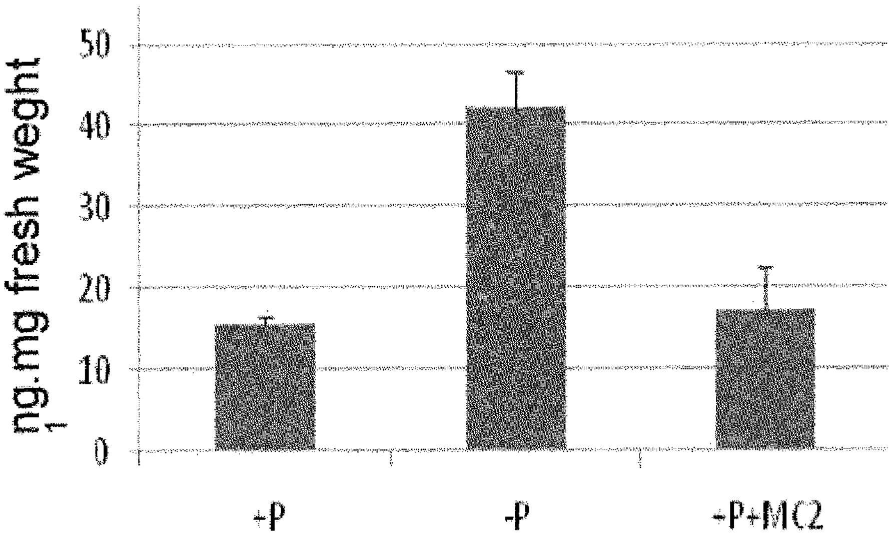

FIG. 11: Iron content determined by ICP-OES. Plants were grown in high phosphate medium, low phosphate medium, or high phosphate medium supplied with MC2 (5 μM).

Figure 12:
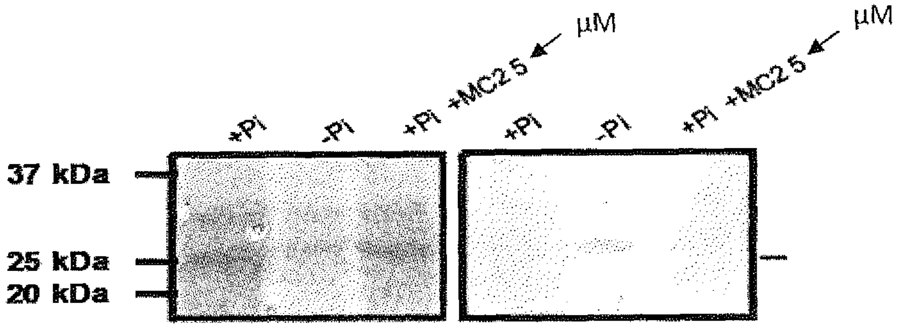

FIG. 12: Western blot of plant ferritin on protein extracts from leaves of plants grown in high phosphate medium, low phosphate medium, or high phosphate medium supplied with MC2 (5 μM). 25 μg of total protein were loaded per line.

Figure 13:
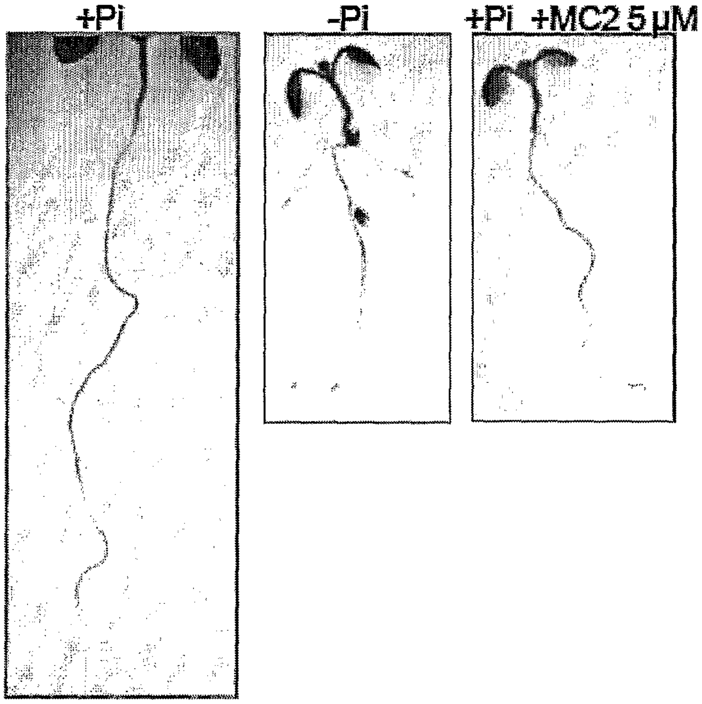

FIG. 13: Histochemical localisation of the GUS activity in root tip of IRT1 grown in high phosphate medium (500 μM) supplied with MC2 (5 μM) or grown in low phosphate medium.

Figure 14:
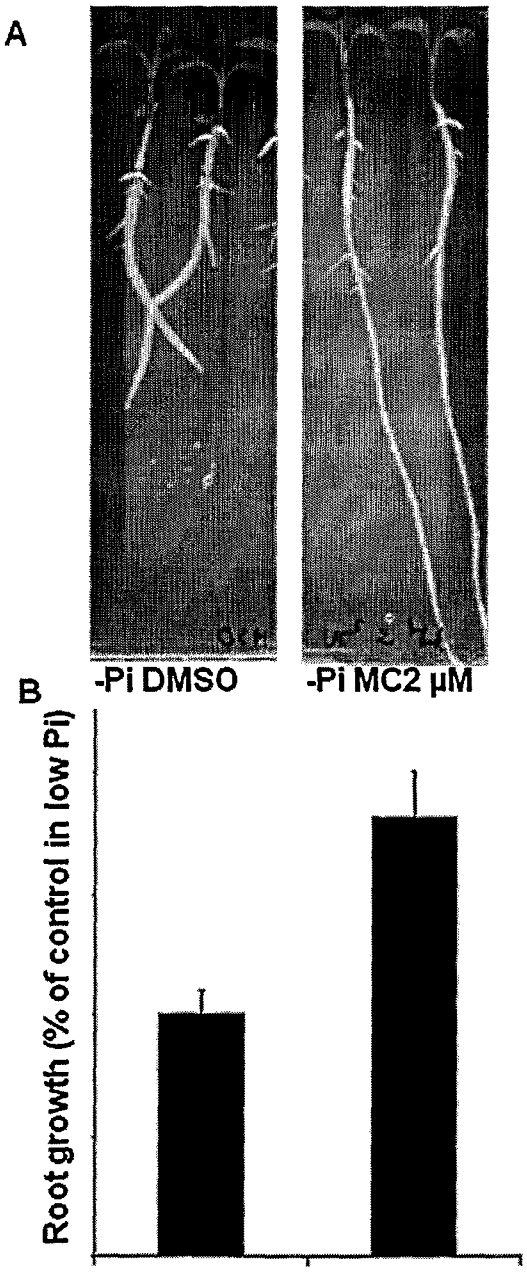

FIG. 14: Root growth of *Medicago truncatula* plants, in a phosphate deficient medium, supplied or not with MC2.

EXAMPLES

In response to phosphate starvation, a large number of physiological and molecular modifications can be observed in plants:

1. The phosphate influx is increased due to the overexpression of phosphate transporter genes of the PHT family and the increase in phosphatase activity.
2. The primary root growth is arrested but it is not due to an inhibition of meristematic activity.
3. The phosphate starvation induces a stress response
4. The lipid metabolism is modified
5. The transport and the accumulation of iron is modified.

The inventors have used several techniques and different markers to evaluate all these physiological and molecular modifications, and to characterize MC2/MC2 analogues effects in details.

Materials and Methods

Cell Lines Used in this Study pPHT1;4::GUS (DCJ 10) cell line is as described by Misson et al. (Misson et al., 2004). This cell line expresses the GUS reporter under the control of the promoter of the pht1;4 gene.

pPLDZ2:GUS-GFP cell line is as described by Cruz-Ramirez et al. (Cruz-Ramirez et al., 2006), and expressed a GUS-GFP fusion under the control of the pldz2 promoter.

pMGD3:GUS cells are as described by Kobayashi et al. (Kobayashi et al., 2004). In these cells, the GUS reporter is expressed under the control of the mgd3 promoter.

pIRT1:GUS cells were obtained as described by Vert et al. (Vert et al., 2002) and carry a irt1 promoter-GUS fusion.

pCycB1;1:GUS cell line is as described by Colón-Carmona et al. (Colon-Carmona et al., 1999), and expresses the GUS reporter under the control of the promoter of the cyclin B1 gene.

8'G cell line was obtained as follows: for the PHT1;4 promoter fusion, a 2 kb region upstream of the ORF of PHT1;4 was cloned in the vector pENTR/D-TOPO (pENTRT™/D-TOPO® Cloning Kit, ref. K2400-20, Invitrogen) and transferred to pKGWFS7 (Karimi et al., 2002) by recombination using Gateway BP (Gateway® BP Clonase® enzyme mix, ref. 11789-013, Invitrogen) and LR Clonase enzyme mixes (LR Clonase® II Plus enzyme, ref. 12538-120, Invitrogen), respectively, to produce the pPHT1;4:GUS-GFP gene fusion. This fusion was then introduced into the *Arabidopsis* genome via the *Agrobacterium*-mediated transformation system (Logemann et al., 2006).

All these cell lines are derived from *A. thaliana*.

Growth Conditions

Seeds were surface-sterilized and sown on petri dishes containing MS/10 medium (0.15 mM $MgSO_4$, 2.1 mM $NH_4NO_3$,1.9 mM $KNO_3$, 0.5 or 0.005 mM $NaH_2PO_4$, 0.3 mM $CaCl_2$, 0.5 μM KI, 10 μM Fe, 10 μM $H_3BO_3$, 10 μM $MnSO_4$, 3 μM $ZnSO_4$, 0.01 μM $CuSO_4$, 0.01 μM $CoCl_2$, 0.1 μM $Na_2MoO_4$, 2 μM EDTA, 0.03 μM thiamine, 0.24 μM pyridoxine, 0.4 μM nicotinic acid, 55 μM inositol, 14 mM MES (pH 5.8), 0.5% sucrose and 0.8% agar. In the Pi deficient medium, NaCl (0.5 mM) was used to replace the equivalent amount of sodium provided by $NaH_2PO_4$. After 3 days at 4° C., the plates were placed in a vertical position and plants were grown for 10 days in a culture chamber under a 14 h light/10 h dark regime (22/18° C., 150 μEm-2s-1).

Gus Staining

Plants were examined for GUS activity by dipping the samples in a GUS staining solution (50 mM sodium phosphate buffer pH 7.0; 0.01% Triton X-100, 1 mM $K_3Fe(CN)_6$, 1 mM $K_4Fe(CN)_6$, 1 mg/ml 5-dromo-4-chloro-3-indolyl (3-D-GLUCURONIDE (X-Gluc A) and incubated at 37° C. over-night. After staining, the plants were fixed 2 hours in 50 mM sodium phosphate buffer pH 7.0; 1% glutaraldehyde; 4% formaldehyde.

Starch Staining

Leaves were immersed in ethanol (96%) for 6 h to remove pigment and stained with Lugol solution (Fluka) for 30 min to make the starch granules visible.

Anthocyanins Content Analysis

Anthocyanins were extracted with propanol:HCl:$H_2O$ (81:1:18) for 5 min at room temperature and 3 min at 100° C. Samples are centrifuged for 10 min at 4° C. Supernatants were collected and absorption measured at 530 nM and 652 nM. Anthocyanin content was calculated as A530-2.2A652 (Lange et al., 1971).

Measurement of the Free Cellular Pi Content

Roots (10 mg) and leaves (25 mg) were pooled, weighed, ground in liquid nitrogen, re-suspended and homogenized in 250 μl of MES buffer (0.7 M, pH 5.8). Three replicates were performed for each experiment. After 5 min of centrifugation, the supernatant was recovered. Phosphate content was measured using the malachite green method as described (Delhaize and Randall, 1995). One hundred and fifty microliters of molybdate solution (17.55 g/l $(NH_4)_6Mo_7$, $4H_2O$, 2M $H_2SO_4$) were added to the sample (50 μl) diluted in water (700 μl). Ten minutes later, 150 μl of green malachite solution (3.5 g/l polyvinylic alcohol, 0.35 g/l malachite green) were then added. Measurements were carried out at 610 nm after 2 h. Concentrations were calculated using a calibration curve (performed with a$KH_2PO_4$ solution) and expressed per fresh weight.

Western Blot

After SDS-PAGE in a 12% acrylamide gel and transfer onto a nitrocellulose membrane, ferritin was immunodetected with a primary rabbit polyclonal antibody against AtFER1 and a secondary goat antirabbit antibody conjugated with alkaline phosphatase.

ICP DES

Fresh leaves from in vitro 10-day-old plants (around 50 mg fresh material) were mineralized in 14% $HNO_3$ in a microwave system (MarsX, CEM) for the determination of macro- and microelements by inductively coupled plasma optical emission spectrometry (ICP OES Vista MPX, Varian).

Example 1

In Response to MC2, the Phosphate Influx is Increased Due to the Overexpression of Phosphate Transporter Genes of the PHT Family and the Increase In Phosphatase Activity Chemical genetic screen was based on PHT1;4 expression using the line pPHT1;4::GUS (Misson et al., 2004). This gene is not expressed in high phosphate medium and is strongly induced in response to phosphate starvation. The inventors have isolated a molecule, called MC2, which can induce the expression of PHT1;4 even if plant grown on high phosphate medium (FIG. 2). The formula of MC2 is the following:

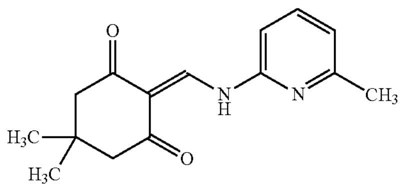

To evaluate if this expression interferes with phosphate content, phosphate content was analyzed in different conditions: high phosphate medium (+Pi), low phosphate medium (−Pi) and high phosphate medium+MC2, 5 μM (+Pi, +MC2 5 μM). The MC2 treatment induced a phosphate accumulation in leaves and in roots (two times more compared to the control condition) (FIG. 3). This phosphate accumulation can be easily explained by the overexpression of the phosphate transporter.

In response to phosphate deficiency, plants are able to secrete phosphatase in soil in order to remobilize phosphate from soil. Phosphatase activity assays showed that in response to phosphate starvation, phosphate activity is largely increased. MC2 mimics phosphate starvation effect inducing phosphatase activity (FIG. 4).

Example 2

The Primary Root Growth is Arrested but it is not Due to an Inhibition of Meristematic Activity In response to phosphate starvation, the primary root growth is inhibited (Svistoonoff et al., 2007). In response to the MC2 molecule, the primary root growth is also arrested in a dose dependent manner (FIG. 5).

Primary root growth arrest is partially due to the inhibition of meristematic activity. The expression of Cycline B1 (CycB1) gene is a good marker of meristematic activity. The expression of this gene was measured in response to high phosphate medium (+Pi), low phosphate medium (−Pi) and high phosphate medium+MC2, 5 μM (+Pi, +MC2 5 μM). In response to phosphate deficiency, CycB1 is less expressed. Suprisingly, in response to MC2, the meristematic activity is not reduced (FIG. 6). Thus, it can be concludes that the primary root growth inhibition observed in response to the molecule is not due to inhibition of the meristematic activity.

Example 3

The Stress Response

In response to phosphate starvation, plant stress responses are also induced, such as starch and anthocyanins accumulations. The effect of MC2 on the accumulation of these two compounds was analyzed.

After Lugol staining, starch accumulation appeared as dark blue vesicles in cells. In response to phosphate deficiency, starch is strongly accumulated (FIG. 7). The same response was obtained after MC2 treatment.

Anthocyanins accumulation was analyzed in vitro by a spectroscopic assay. Phosphate starvation, as well as MC2 treatment, induced a strong accumulation of anthocyanins (FIG. 8).

Example 4

Modifications of the Lipid Metabolism

In response to phosphate starvation, the lipid metabolism is modified (Benning and Ohta, 2005). Plants preferentially synthesize sulpho- and galacto-lipids instead of phospholipids. Several enzymes are involved in this remobilisation. From previous studies in the lab (Misson et al., 2005), it is known that two genes respectively encoding MGD3 and PLDζ2 enzyme (Cruz-Ramirez et al., 2006; Yamaryo et al., 2008) are strongly induced in response to phosphate starvation. The inventors have hence analyzed the expression of these two gene in high phosphate medium (+Pi), low phosphate medium (−Pi) and high phosphate medium+MC2, 5 μM (+Pi, +MC2 5 μM) conditions.

MGD3 is not express in high phosphate medium. It has to be noticed that this gene is strongly expressed in response to phosphate starvation and in response to MC2 treatment (FIG. 9).

As MGD3, PLDζ2 gene is not expressed in high phosphate medium but strongly expressed in response to starvation and MC2 treatment (FIG. 10). From this experiment, it appears that MC2 mimics phosphate starvation effects concerning the lipid metabolism.

Example 5

The Transport and the Accumulation of Iron is Modified Too

From previous study in the lab, it is known that in response to phosphate starvation, iron is accumulated in cells inducing ferritin accumulation (Hirsch et al., 2006). To determine MC2 effect on iron metabolism, the iron content was quantified by ICP-OES (FIG. 11), accumulation of ferritin was analyzed by Western Blot (FIG. 12) and finally IRT1 gene expression was analyzed, since this gene encodes an iron transporter (FIG. 12).

The ICP-OES analysis of iron content showed that in response to phosphate starvation Iron is strongly accumulated but not after MC2 treatment (FIG. 11). Western blot analysis of ferritin accumulation revealed that ferritin is accumulated in response to phosphate starvation but not in response to MC2 treatment (FIG. 12).

IRT1 transports Iron from outside to inside the plant. In response to phosphate starvation, this transporter is not expressed because iron is strongly accumulated. The plant does not need import of iron (FIG. 13). Surprisingly, MC2 treatment inhibits IRT1 expression even if iron is not accumulated in plant.

A summary of the effects of MC2 on plants is provided in Table 2.

Example 6

Effects of MC2 Analogues on Plants

The effects described in the preceding examples have also been tested for a number of analogues of the MC2 molecule.

Surprisingly, it appeared that for almost all these analogues, only part of these effects were observed. Indeed, some analogues can specifically impact the lipids synthesis, while others have an impact on iron transporter, plant growth, etc.

For example, the analogues #21, #29, #30, #31, #41, #42, #45 impact specifically the lipid metabolism inducing PLD□2 and MGD3. The inventors also isolated analogues that are able to induced PHT 1;4 expression without altering the root growth: #1, #5, #7, #11, #14, #20, #22, #27, #43, #44, #47.

All the results, together with the formulas of the analogues, are summarized in Table 3 below.

Example 7

Effect of MC2 on Growth of Roots in a Phosphate Deficient Medium

*Medicago truncatula* seeds were surface-sterilized as follow: soaking in concentrated sulphuric acid for 10 min, rinsing three times with sterile distilled water, soaking in 10% bleach/0.1% Tween 20 solution for 10 min with gentle agitation and finally by rinsing seeds three times with sterile distilled water. Seeds were germinated 48 h in dark. Then, plants were transferred in Murashige and Skoog (MS)/10 medium (0.15 mM $MgSO_4$, 2.1 mM $NH_4NO_3$, 1.9 mM $KNO_3$, 0.5 or 0.005 mM $NaH_2PO_4$, 0.3 mM $CaCl_2$, 0.5 μM KI, 10 μM Fe, 10 μM $H_3BO_3$, 10 μM $MnSO_4$, 3 μM $ZnSO_4$, 0.01 μM $CuSO_4$, 0.01 μM $CoCl_2$, 0.1 μM $Na_2MoO_4$, 2 μM EDTA, 0.03 μM thiamine, 0.24 μM pyridoxine, 0.4 μM nicotinic acid, 55 μM inositol, 14 mM MES (pH 5.8), 0.5% sucrose and 0.8% agar) supplied with phosphate (500 μM) or depleted with phosphate (10 μM) with or without MC2 molecule (5 μM). In the phosphate (Pi) deficient medium, NaCl (0.5 mM) was used to replace the equivalent amount of sodium provided by $NaH_2PO_4$.). Plants were maintained 10 days under a 14 h light/10 h 150 $\mu m^{-2}s^{-1}$ dark regime with a temperature of 22/18° C. for light/dark phases in a phytotron. The results, reported on FIG. 14, show that the growth of roots of the plants in a Pi deficient medium is improved in the presence of MC2 and illustrates the reduction of the need for phosphate fertilizer when the plant is supplied with MC2.

TABLE 2

Impact of phosphate, phosphate deficiency and MC2 on several parameters of plant growth.

| Reference | Name | Formula | Root Growth | 8'G::GUS | PLDz::GUS | IRT1::GUS |
|---|---|---|---|---|---|---|
| | | +P | 100 | − | − | + |
| | | −P | 20 | + | + | − |
| 5521417 | MC2 | 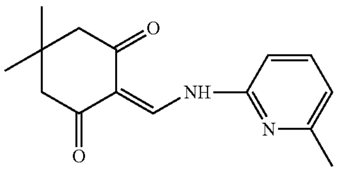 | 51 | + | + | − |

| Reference | Name | Formula | MGD3::GUS | CycB::GUS | Starch | Antho |
|---|---|---|---|---|---|---|
| | | +P | − | + | − | 46 |
| | | −P | + | − | + | 1008 |
| 5521417 | MC2 | 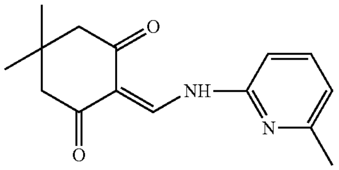 | + | + | + | 454 |

Root growth: expressed as a percentage having regard to a control;

8'G::GUS: follow-up of the expression of the phosphate transporter PHT1;4;

PLDz::GUS: follow-up of the expression of the gene encoding phopholipase Dz2;

IRT1::GUS: follow-up of the expression of the gene encoding the iron transporter IRT1;

MGD3::GUS follow-up of the expression of the gene encoding the enzyme MGD3;

CycB1::GUS follow-up of the expression of the gene encoding Cyclin B1;

Starch: accumulation of starch;

Antho: accumulation of anthocyanes.

TABLE 3
Impact of MC2 analogues on plant growth.
| Reference | Name | Formula | Root Growth | 8'G::GUS | PLDz::GUS | IRT1::GUS |
|---|---|---|---|---|---|---|
| 5521417 | MC2 | 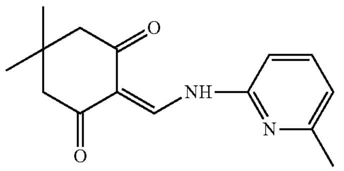 | 51 | + | + | − |
| 5220640 | #1 | 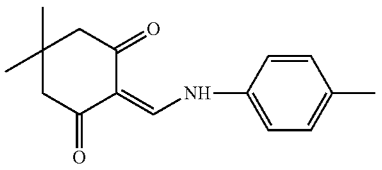 | 64 | + | + | + |
| 5220641 | #2 | 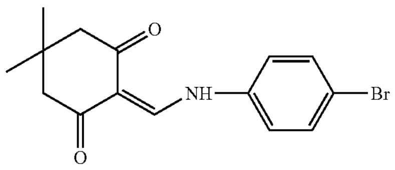 [SMILES: CC1(C)CC(=O)C(=CNc2ccc(Br)cc2)C(=O)C1] | 59 | + | + | + |
| 5249268 | #3 | 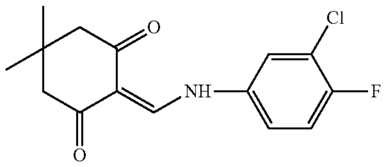 [SMILES: CC1(C)CC(=O)C(=CNc2ccc(F)c(Cl)c2)C(=O)C1] | 41 | + | + | + |
| 5482362 | #4 | 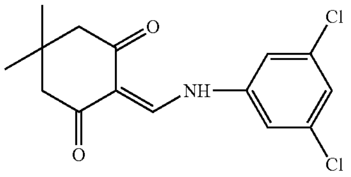 [SMILES: CC1(C)CC(=O)C(=CNc2cc(Cl)cc(Cl)c2)C(=O)C1] | 50 | + | + | − |
| 5484851 | #5 | 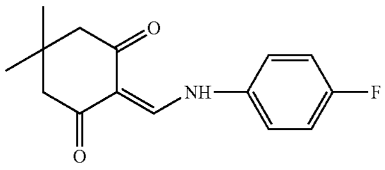 [SMILES: CC1(C)CC(=O)C(=CNc2ccc(F)cc2)C(=O)C1] | 73 | + | + | + |
| 5486289 | #6 | 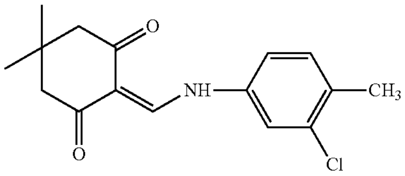 | 53 | + | − | − |
| 54911335 | #7 | 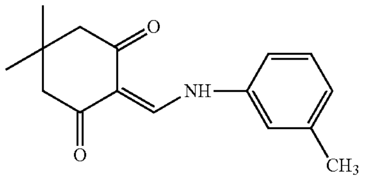 | 75 | + | − | + |

TABLE 3-continued
| Impact of MC2 analogues on plant growth. | | | | | | |
|---|---|---|---|---|---|---|
| 5491651 | #8 | 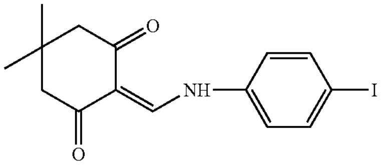 [SMILES: CC1(C)CC(=O)C(=CNc2ccc(I)cc2)C(=O)C1] | 56 | − | − | + |
| 5492143 | #9 | 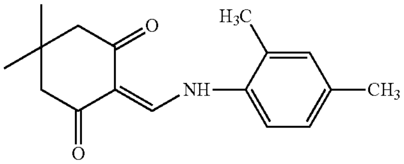 | 71 | + | + | + |
| 5492676 | #10 | 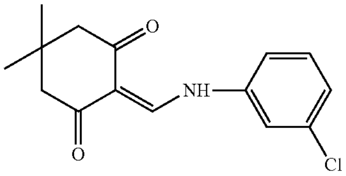 [SMILES: CC1(C)CC(=O)C(=CNc2cccc(Cl)c2)C(=O)C1] | 41 | + | + | + |
| 5493194 | #11 | 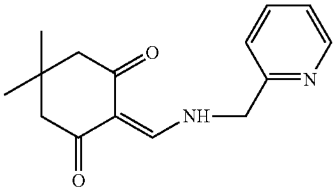 [SMILES: CC1(C)CC(=O)C(=CNCc2ccccn2)C(=O)C1] | 63 | + | + | + |
| 5493512 | #12 | 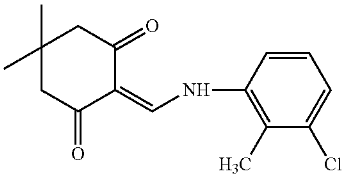 [SMILES: Cc1c(Cl)cccc1NC=C1C(=O)CC(C)(C)CC1=O] | 57 | + | + | + |
| 5521400 | #13 | 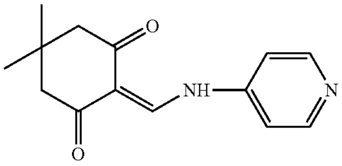 [SMILES: CC1(C)CC(=O)C(=CNc2ccncc2)C(=O)C1] | 42 | + | + | + |
| 5630089 | #14 | 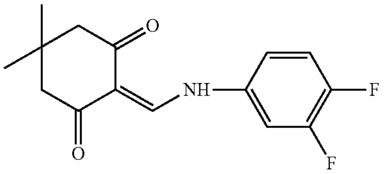 [SMILES: CC1(C)CC(=O)C(=CNc2ccc(F)c(F)c2)C(=O)C1] | 61 | + | + | + |
| 5666610 | #15 | 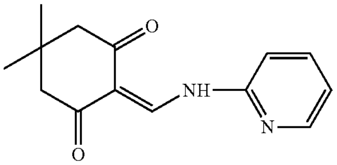 [SMILES: CC1(C)CC(=O)C(=CNc2ccccn2)C(=O)C1] | 40 | + | + | + |

TABLE 3-continued
Impact of MC2 analogues on plant growth.
| | | | | | | |
|---|---|---|---|---|---|---|
| 5666611 | #16 | 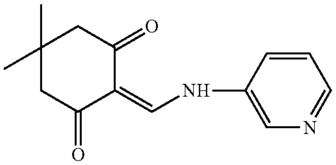 | 40 | + | + | − |
| 5666617 | #17 | 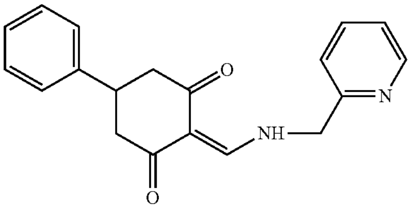 [SMILES: O=C1CC(c2ccccc2)CC(=O)C1=CNCc1ccccn1] | 60 | − | − | − |
| 5691461 | #18 | 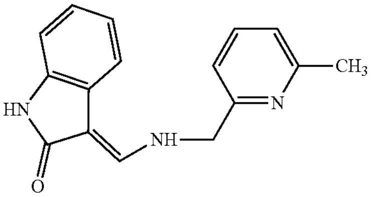 [SMILES: Cc1cccc(CN/C=C2/C(=O)Nc3ccccc32)n1] | 88 | − | − | + |
| 5785319 | #19 | 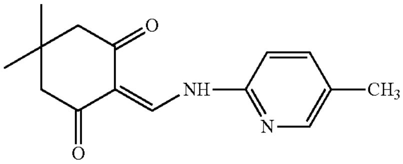 | 47 | + | + | + |
| 5858517 | #20 | 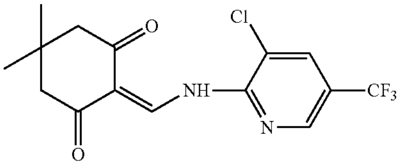 [SMILES: CC1(C)CC(=O)C(=CNc2ncc(C(F)(F)F)cc2Cl)C(=O)C1] | 72 | + | + | + |
| 5963688 | #21 | 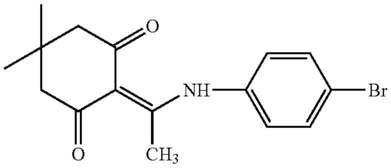 | 93 | − | − | + |
| E621 | #22 | 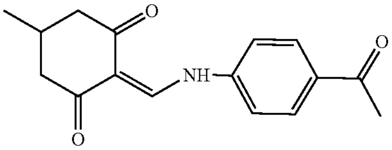 [SMILES: CC(=O)c1ccc(NC=C2C(=O)CC(C)CC2=O)cc1] | 72 | + | + | + |
| AURORA 3525 | #23 | 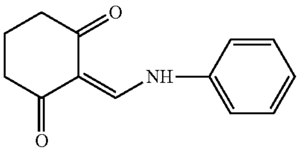 [SMILES: O=C1CCCC(=O)C1=CNc1ccccc1] | 100 | − | − | + |

TABLE 3-continued
| Impact of MC2 analogues on plant growth. | | | | | | |
|---|---|---|---|---|---|---|
| ES113 | #24 | 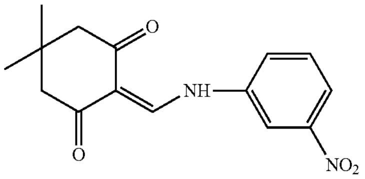 [SMILES: CC1(C)CC(=O)C(=CNc2cccc([N+](=O)[O-])c2)C(=O)C1] | 54 | + | + | + |
| ES188 | #25 | 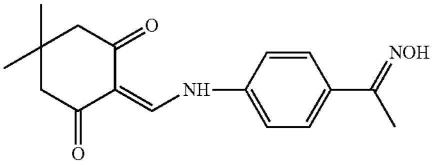 | 63 | + | −/+ | + |
| E228 | #26 | 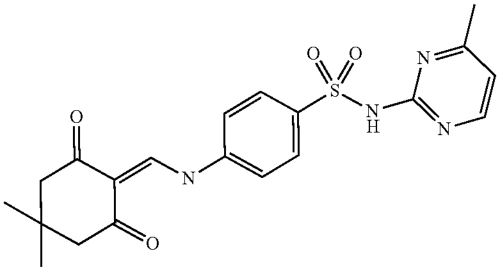 | 6 | ?* | ?* | ?* |
| ES292 | #27 | 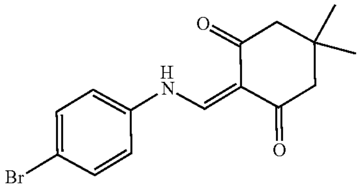 | 98 | + | + | + |
| ST927 | #28 | 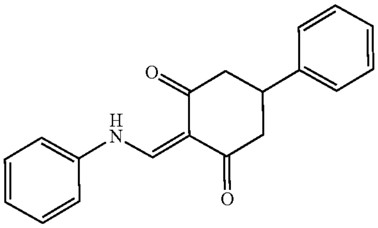 | 100 | + | − | + |
| ST981 | #29 | 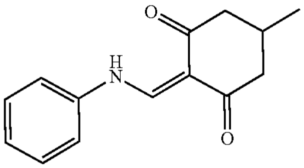 | 85 | − | + | + |
| ST3897 | #30 | 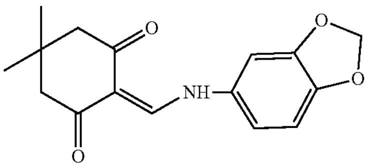 [SMILES: CC1(C)CC(=O)C(=CNc2ccc3c(c2)OCO3)C(=O)C1] | 65 | − | + | + |

TABLE 3-continued
| Impact of MC2 analogues on plant growth. | | | | | | |
|---|---|---|---|---|---|---|
| ST2248 | #31 | 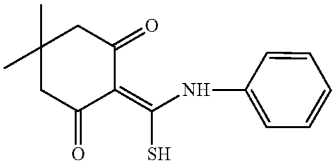 [SMILES: CC1(C)CC(=O)C(=C(S)Nc2ccccc2)C(=O)C1] | 89 | − | − | + |
| E1968 | #32 | 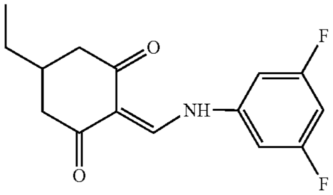 [SMILES: CCC1CC(=O)C(=CNc2cc(F)cc(F)c2)C(=O)C1] | 13 | + | + | + |
| CB285 | #33 | 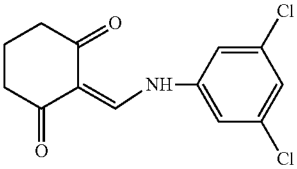 [SMILES: O=C1CCCC(=O)C1=CNc1cc(Cl)cc(Cl)c1] | 59 | + | + | + |
| ES140 | #34 | 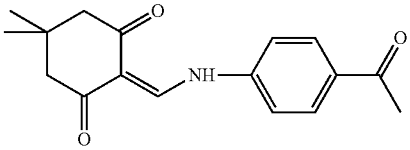 [SMILES: CC(=O)c1ccc(NC=C2C(=O)CC(C)(C)CC2=O)cc1] | 59 | + | + | + |
| CB395 | #35 | 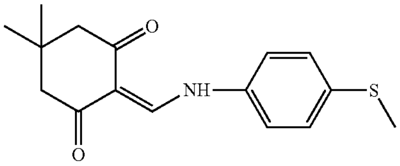 | 60 | −/+ | + | + |
| SR97 | #36 | 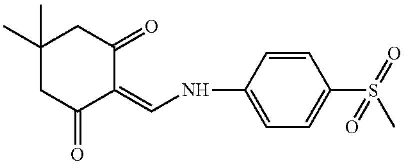 [SMILES: CC1(C)CC(=O)C(=CNc2ccc(S(C)(=O)=O)cc2)C(=O)C1] | 58 | + | + | + |
| E1725 | #37 | 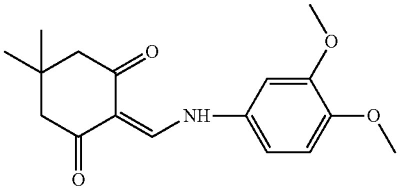 | 69 | + | + | + |
| E1829 | #38 | 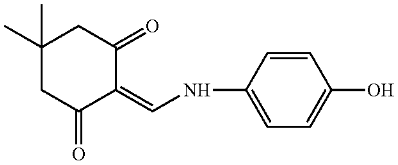 [SMILES: CC1(C)CC(=O)C(=CNc2ccc(O)cc2)C(=O)C1] | 60 | + | − | + |

TABLE 3-continued
| Impact of MC2 analogues on plant growth. | | | | | | |
|---|---|---|---|---|---|---|
| DW196 | #39 | 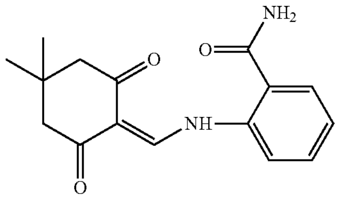 [SMILES: CC1(C)CC(=O)C(=CNc2ccccc2C(N)=O)C(=O)C1] | 60 | + | + | + |
| 7W-0874 | #40 | 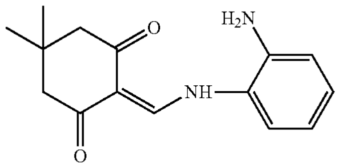 [SMILES: CC1(C)CC(=O)C(=CNc2ccccc2N)C(=O)C1] | 85 | − | − | + |
| 7H-940 | #41 | 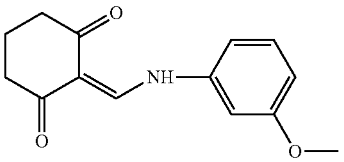 [SMILES: COc1cccc(NC=C2C(=O)CCCC2=O)c1] | 65 | − | − | + |
| AI-559/ 36942007 | #42 | 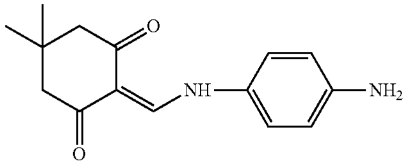 [SMILES: CC1(C)CC(=O)C(=CNc2ccc(N)cc2)C(=O)C1] | 68 | − | + | + |
| 10N-521S | #43 | 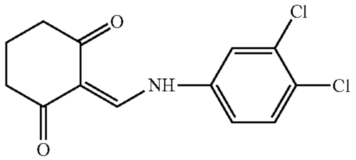 [SMILES: O=C1CCCC(=O)C1=CNc1ccc(Cl)c(Cl)c1] | 67 | + | + | + |
| 10N-523S | #44 | 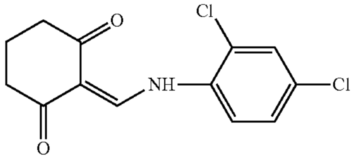 [SMILES: O=C1CCCC(=O)C1=CNc1ccc(Cl)cc1Cl] | 68 | + | + | + |
| 10N-524S | #45 | 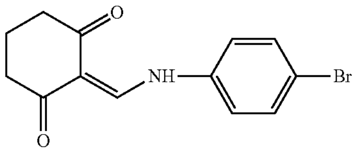 [SMILES: O=C1CCCC(=O)C1=CNc1ccc(Br)cc1] | 67 | − | + | + |
| 10N-525S | #46 | 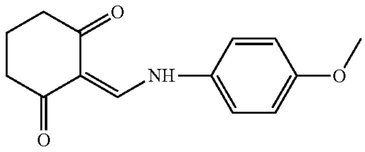 | 70 | − | − | + |

TABLE 3-continued
Impact of MC2 analogues on plant growth.
| Reference | Name | Formula | MGD3::GUS | CycB::GUS | Starch | Antho |
|---|---|---|---|---|---|---|
| 5W-0900 | #47 | 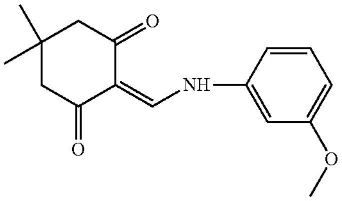 [SMILES: COc1cccc(NC=C2C(=O)CC(C)(C)CC2=O)c1] | 70 | + | + | + |
| 5521417 | MC2 | 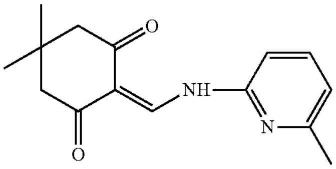 | + | + | + | 454 |
| 5220640 | #1 | 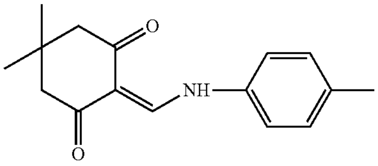 | − | + | + | 274 |
| 5220641 | #2 | 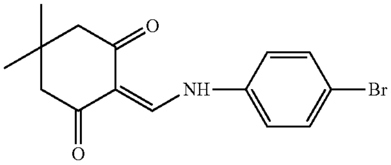 [SMILES: CC1(C)CC(=O)C(=CNc2ccc(Br)cc2)C(=O)C1] | − | + | − | 258 |
| 5249268 | #3 | 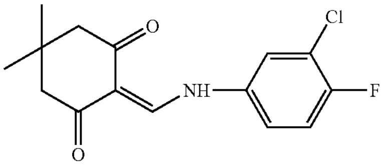 [SMILES: CC1(C)CC(=O)C(=CNc2ccc(F)c(Cl)c2)C(=O)C1] | + | + | + | 806 |
| 5482362 | #4 | 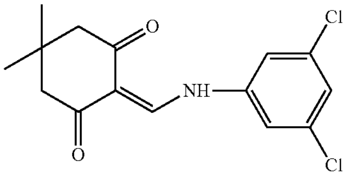 [SMILES: CC1(C)CC(=O)C(=CNc2cc(Cl)cc(Cl)c2)C(=O)C1] | + | − | + | 210 |
| 5484851 | #5 | 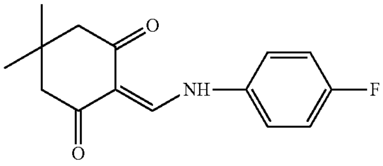 [SMILES: CC1(C)CC(=O)C(=CNc2ccc(F)cc2)C(=O)C1] | − | + | + | 110 |
| 5486289 | #6 | 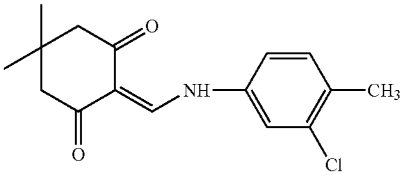 | + | + | + | + |

TABLE 3-continued
| Impact of MC2 analogues on plant growth. | | | | | | |
|---|---|---|---|---|---|---|
| 54911335 | #7 | 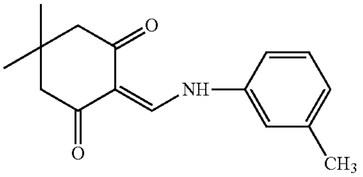 | + | + | + | 172 |
| 5491651 | #8 | 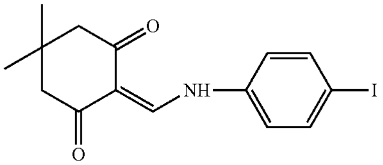 [SMILES: CC1(C)CC(=O)C(=CNc2ccc(I)cc2)C(=O)C1] | − | + | − | 37 |
| 5492143 | #9 | 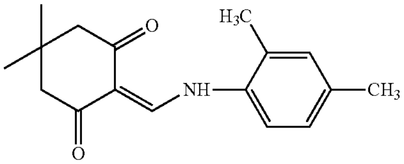 | + | + | − | 130 |
| 5492676 | #10 | 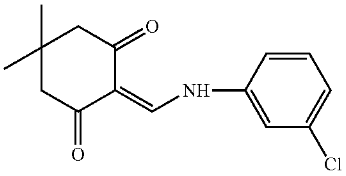 [SMILES: CC1(C)CC(=O)C(=CNc2cccc(Cl)c2)C(=O)C1] | + | + | − | 225 |
| 5493194 | #11 | 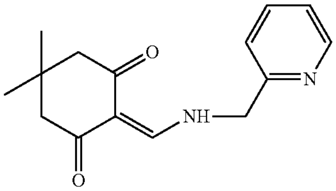 [SMILES: CC1(C)CC(=O)C(=CNCc2ccccn2)C(=O)C1] | + | + | + | 163 |
| 5493512 | #12 | 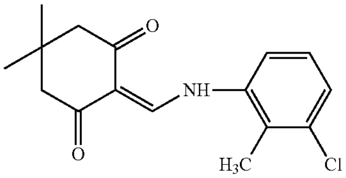 [SMILES: Cc1c(Cl)cccc1NC=C1C(=O)CC(C)(C)CC1=O] | + | + | + | 850 |
| 5521400 | #13 | 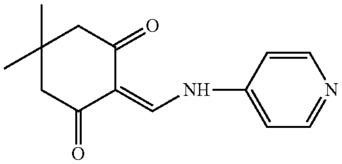 [SMILES: CC1(C)CC(=O)C(=CNc2ccncc2)C(=O)C1] | + | + | + | 513 |
| 5630089 | #14 | 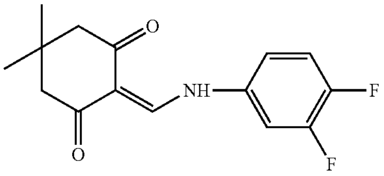 | + | + | + | 150 |

TABLE 3-continued
Impact of MC2 analogues on plant growth.
| | | | | | | |
|---|---|---|---|---|---|---|
| 5666610 | #15 | 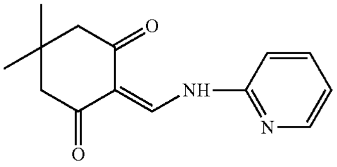 [SMILES: CC1(C)CC(=O)C(=CNc2ccccn2)C(=O)C1] | + | + | + | 283 |
| 5666611 | #16 | 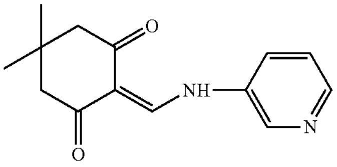 [SMILES: CC1(C)CC(=O)C(=CNc2cccnc2)C(=O)C1] | + | – | + | 431 |
| 5666617 | #17 | 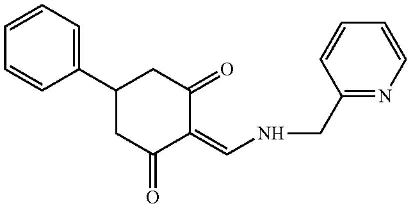 [SMILES: O=C1CC(c2ccccc2)CC(=O)C1=CNCc1ccccn1] | + | – | + | 408 |
| 5691461 | #18 | 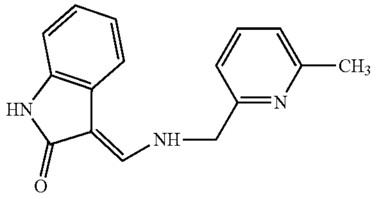 [SMILES: Cc1cccc(CN/C=C2/C(=O)Nc3ccccc32)n1] | – | + | – | 195 |
| 5785319 | #19 | 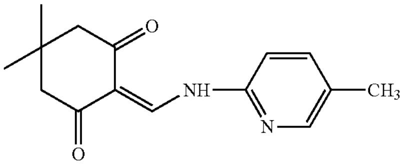 | + | + | + | 193 |
| 5858517 | #20 | 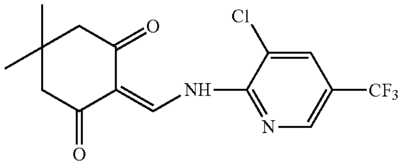 [SMILES: CC1(C)CC(=O)C(=CNc2ncc(C(F)(F)F)cc2Cl)C(=O)C1] | + | + | – | 142 |
| 5963688 | #21 | 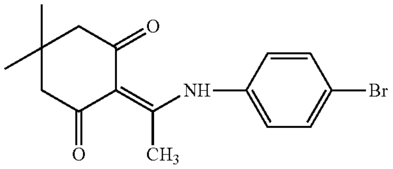 [SMILES: CC(Nc1ccc(Br)cc1)=C1C(=O)CC(C)(C)CC1=O] | – | + | – | 146 |
| E621 | #22 | 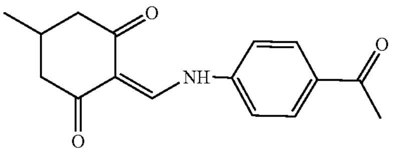 [SMILES: CC(=O)c1ccc(NC=C2C(=O)CC(C)CC2=O)cc1] | – | | – | 101 |

TABLE 3-continued
Impact of MC2 analogues on plant growth.
| | | | | | |
|---|---|---|---|---|---|
| AURORA 3525 | #23 | 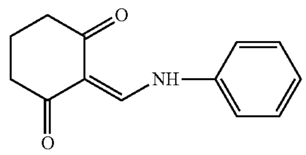 [SMILES: O=C1CCCC(=O)C1=CNc1ccccc1] | + | − | 42 |
| ES113 | #24 | 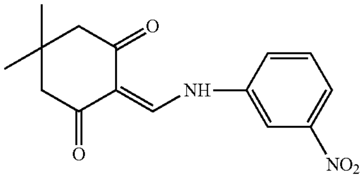 [SMILES: CC1(C)CC(=O)C(=CNc2cccc([N+](=O)[O-])c2)C(=O)C1] | + | − | 240 |
| ES188 | #25 | 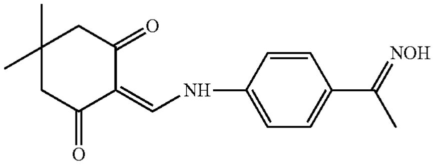 | + | + | 405 |
| E228 | #26 | 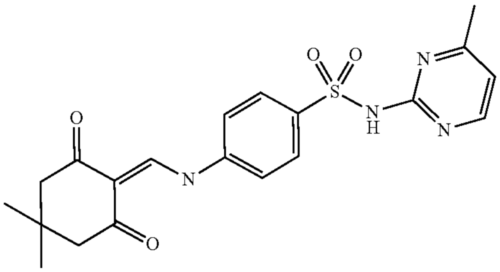 | ?* | + | 640 |
| ES292 | #27 | 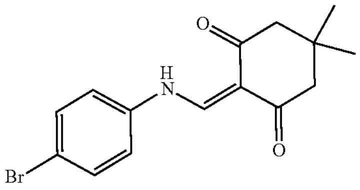 | + | − | 43 |
| ST927 | #28 | 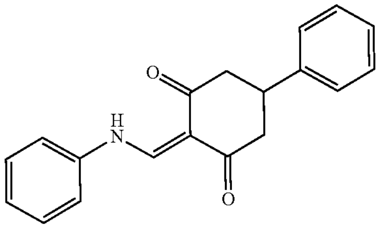 | + | + | 247 |
| ST981 | #29 | 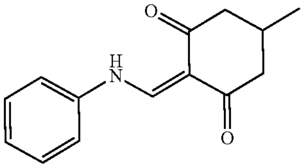 | + | + | 146 |
| ST3897 | #30 | 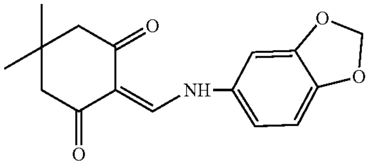 [SMILES: CC1(C)CC(=O)C(=CNc2ccc3c(c2)OCO3)C(=O)C1] | + | + | 189 |

TABLE 3-continued
Impact of MC2 analogues on plant growth.
| | | | | | |
|---|---|---|---|---|---|
| ST2248 | #31 | 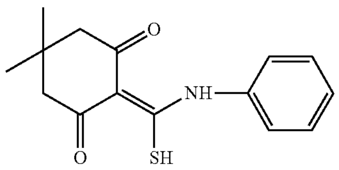 [SMILES: CC1(C)CC(=O)C(=C(S)Nc2ccccc2)C(=O)C1] | + | − | 62 |
| E1968 | #32 | 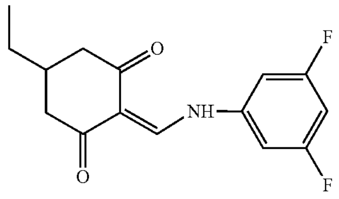 [SMILES: CCC1CC(=O)C(=CNc2cc(F)cc(F)c2)C(=O)C1] | − | + | 103 |
| CB285 | #33 | 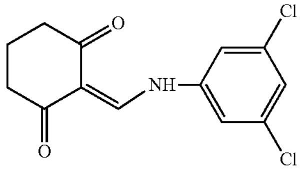 [SMILES: O=C1CCCC(=O)C1=CNc1cc(Cl)cc(Cl)c1] | −/+ | + | 167 |
| ES140 | #34 | 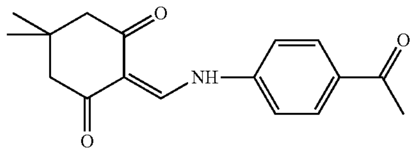 [SMILES: CC(=O)c1ccc(NC=C2C(=O)CC(C)(C)CC2=O)cc1] | + | + | 289 |
| CB395 | #35 | 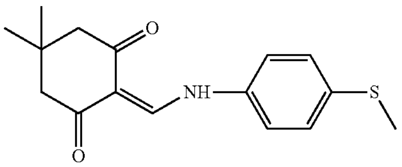 | + | + | 208 |
| SR97 | #36 | 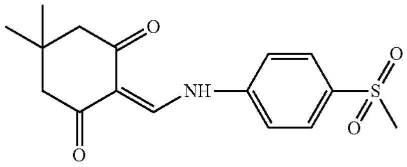 [SMILES: CC1(C)CC(=O)C(=CNc2ccc(S(C)(=O)=O)cc2)C(=O)C1] | + | + | 235 |
| E1725 | #37 | 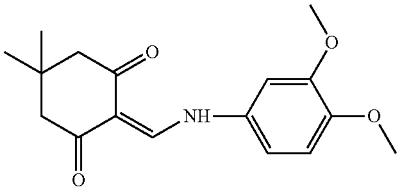 | + | + | 204 |
| E1829 | #38 | 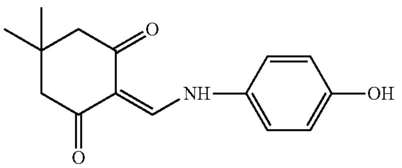 [SMILES: CC1(C)CC(=O)C(=CNc2ccc(O)cc2)C(=O)C1] | + | + | 206 |

TABLE 3-continued
| Impact of MC2 analogues on plant growth. | | | | | |
|---|---|---|---|---|---|
| DW196 | #39 | 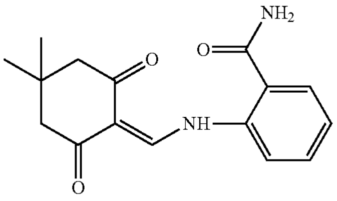 [SMILES: CC1(C)CC(=O)C(=CNc2ccccc2C(N)=O)C(=O)C1] | + | + | 183 |
| 7W-0874 | #40 | 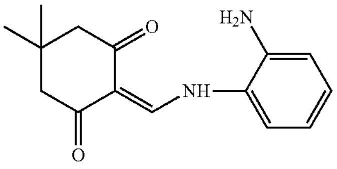 [SMILES: CC1(C)CC(=O)C(=CNc2ccccc2N)C(=O)C1] | + | − | 65 |
| 7H-940 | #41 | 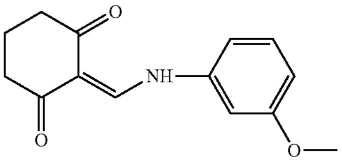 [SMILES: COc1cccc(NC=C2C(=O)CCCC2=O)c1] | + | − | 111 |
| AI-559/ 36942007 | #42 | 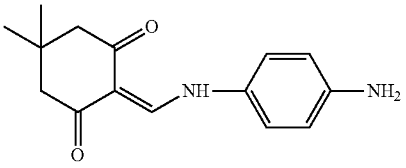 [SMILES: CC1(C)CC(=O)C(=CNc2ccc(N)cc2)C(=O)C1] | + | − | 226 |
| 10N-521S | #43 | 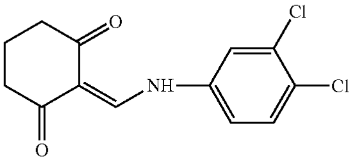 [SMILES: O=C1CCCC(=O)C1=CNc1ccc(Cl)c(Cl)c1] | + | − | 186 |
| 10N-523S | #44 | 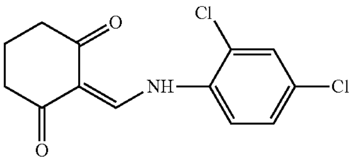 [SMILES: O=C1CCCC(=O)C1=CNc1ccc(Cl)cc1Cl] | + | − | 123 |
| 10N-524S | #45 | 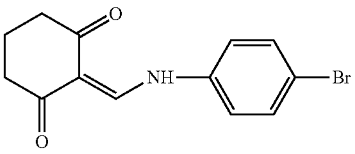 | + | − | 106 |
| 10N-525S | #46 | 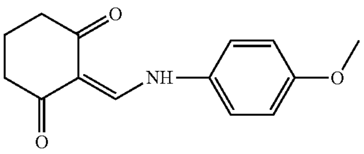 | + | − | 167 |

TABLE 3-continued

| Impact of MC2 analogues on plant growth. | | | | | |
|---|---|---|---|---|---|
| 5W-0900 | #47 | 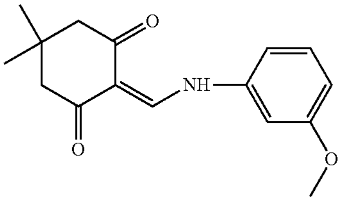 | +/− | + | 324 |

Root growth: expressed as a percentage having regard to a control;
8'G::GUS: follow-up of the expression of the phosphate transporter PHT1;4;
PLDz::GUS: follow-up of the expression of the gene encoding phopholipase Dz2;
IRT1::GUS: follow-up of the expression of the gene encoding the iron transporter IRT1;
MGD3::GUS follow-up of the expression of the gene encoding the enzyme MGD3;
CycB1::GUS follow-up of the expression of the gene encoding Cyclin B1;
Starch: accumulation of starch;
Antho: accumulation of anthocyanes.
*results could not be determined due to the toxicity of this compound.

REFERENCES

Andrianasolo, E. H., Haramaty, L., Vardi, A., White, E., Lutz, R. and Falkowski, P. (2008) Apoptosis-inducing galactolipids from a cultured marine diatom, Phaeodactylum tricornutum. *J Nat Prod,* 71, 1197-1201.

Benning, C. and Ohta, H. (2005) Three enzyme systems for galactoglycerolipid biosynthesis are coordinately regulated in plants. *J Biol Chem,* 280, 2397-2400.

Bruno, A., Rossi, C., Marcolongo, G., Di Lena, A., Venzo, A., Berrie, C. P. and Corda, D. (2005) Selective in vivo anti-inflammatory action of the galactolipid monogalactosyldiacylglycerol. *Eur J Pharmacol,* 524, 159-168.

Chisti, Y. (2007) Biodiesel from microalgae. *Biotechnol Adv,* 25, 294-306.

Colon-Carmona, A., You, R., Haimovitch-Gal, T. and Doerner, P. (1999) Technical advance: spatio-temporal analysis of mitotic activity with a labile cyclin-GUS fusion protein. *Plant J,* 20, 503-508.

Cruz-Ramirez, A., Oropeza-Aburto, A., Razo-Hernandez, F., Ramirez-Chavez, E. and Herrera-Estrella, L. (2006) Phospholipase DZ2 plays an important role in extraplastidic galactolipid biosynthesis and phosphate recycling in *Arabidopsis* roots. *Proc Natl Acad Sci USA,* 103, 6765-6770.

Delhaize, E. and Randall, P. J. (1995) Characterization of a Phosphate-Accumulator Mutant of *Arabidopsis thaliana. Plant Physiol,* 107, 207-213.

Durrett, T. P., Benning, C. and Ohlrogge, J. (2008) Plant triacylglycerols as feedstocks for the production of biofuels. *Plant J,* 54, 593-607.

Hirsch, J., Marin, E., Floriani, M., Chiarenza, S., Richaud, P., Nussaume, L. and Thibaud, M. C. (2006) Phosphate deficiency promotes modification of iron distribution in *Arabidopsis* plants. *Biochimie,* 88, 1767-1771.

Jouhet, J., Marechal, E. and Block, M. A. (2007) Glycerolipid transfer for the building of membranes in plant cells. *Prog Lipid Res,* 46, 37-55.

Karimi, M., Inze, D. and Depicker, A. (2002) GATEWAY vectors for *Agrobacterium*-mediated plant transformation. *Trends Plant Sci,* 7, 193-195.

Kobayashi, K., Awai, K., Takamiya, K. and Ohta, H. (2004) *Arabidopsis* type B monogalactosyldiacylglycerol synthase genes are expressed during pollen tube growth and induced by phosphate starvation. *Plant Physiol,* 134, 640-648.

Lange, H., Shropshire, W. and Mohr, H. (1971) An Analysis of Phytochrome-mediated Anthocyanin Synthesis. *Plant Physiol,* 47, 649-655.

Liguori, L., Marques, B., Villegas-Mendez, A., Rothe, R. and Lenormand, J. L. (2008) Liposomes-mediated delivery of pro-apoptotic therapeutic membrane proteins. *J Control Release,* 126, 217-227.

Logemann, E., Birkenbihl, R. P., Ulker, B. and Somssich, I. E. (2006) An improved method for preparing *Agrobacterium* cells that simplifies the *Arabidopsis* transformation protocol. *Plant Methods,* 2, 16.

Maeda, N., Kokai, Y., Ohtani, S., Sahara, H., Hada, T., Ishimaru, C., Kuriyama, I., Yonezawa, Y., Iijima, H., Yoshida, H., Sato, N. and Mizushina, Y. (2007) Anti-tumor effects of the glycolipids fraction from spinach which inhibited DNA polymerase activity. *Nutr Cancer,* 57, 216-223.

Misson, J., Raghothama, K. G., Jain, A., Jouhet, J., Block, M. A., Bligny, R., Ortet, P., Creff, A., Somerville, S., Rolland, N., Doumas, P., Nacry, P., Herrerra-Estrella, L., Nussaume, L. and Thibaud, M. C. (2005) A genome-wide transcriptional analysis using *Arabidopsis thaliana* Affymetrix gene chips determined plant responses to phosphate deprivation. *Proc Natl Acad Sci USA,* 102, 11934-11939.

Misson, J., Thibaud, M. C., Bechtold, N., Raghothama, K. and Nussaume, L. (2004) Transcriptional regulation and functional properties of *Arabidopsis* Pht1;4, a high affinity transporter contributing greatly to phosphate uptake in phosphate deprived plants. *Plant Mol Biol,* 55, 727-741.

Raghothama, K. G. (1999) Phosphate Acquisition. *Annu Rev Plant Physiol Plant Mol Biol,* 50, 665-693.

Selmair, P. L. and Koehler, P. (2008) Baking performance of synthetic glycolipids in comparison to commercial surfactants. *J Agric Food Chem,* 56, 6691-6700.

Svistoonoff, S., Creff, A., Reymond, M., Sigoillot-Claude, C., Ricaud, L., Blanchet, A., Nussaume, L. and Desnos, T. (2007) Root tip contact with low-phosphate media reprograms plant root architecture. *Nat Genet,* 39, 792-796.

Tjellstrom, H., Andersson, M. X., Larsson, K. E. and Sandelius, A. S. (2008) Membrane phospholipids as a phosphate reserve: the dynamic nature of phospholipid-to-digalactosyl diacylglycerol exchange in higher plants. *Plant Cell Environ,* 31, 1388-1398.

Vert, G., Grotz, N., Dedaldechamp, F., Gaymard, F., Guerinot, M. L., Briat, J. F. and Curie, C. (2002) IRT1, an *Arabidopsis* transporter essential for iron uptake from the soil and for plant growth. *Plant Cell,* 14, 1223-1233.

Yamaryo, Y., Dubots, E., Albrieux, C., Baldan, B. and Block, M. A. (2008) Phosphate availability affects the tonoplast localization of PLDzeta2, an *Arabidopsis thaliana* phospholipase *D. FEBS Lett,* 582, 685-690.

The invention claimed is:

1. A method of growing plants for biofuel or plastid glycolipids production, or for reducing the need for phosphate fertilizer for growing plants, comprising the step of applying a plant additive in a phosphate-deficient cultivation medium of the plants, wherein the plant additive comprises at least one compound selected from the group consisting of MC2, #1-7, #9-17, #19-20, and #22-47 as set forth below:

MC2

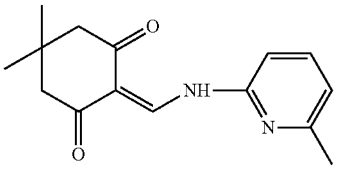

#1

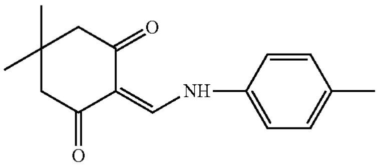

#2

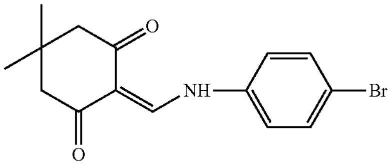

#3

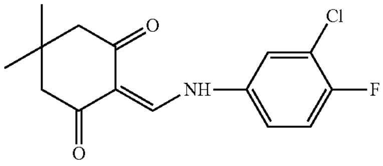

#4

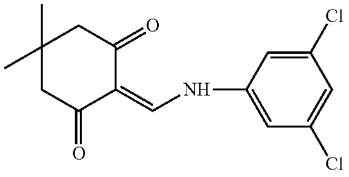

#5

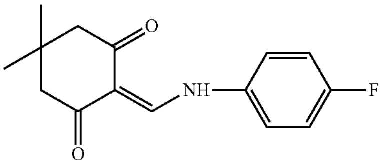

#6

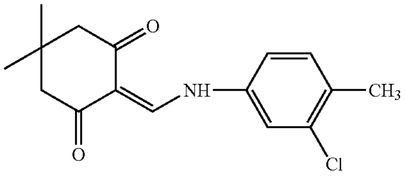

-continued

#7

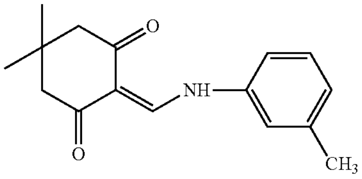

#9

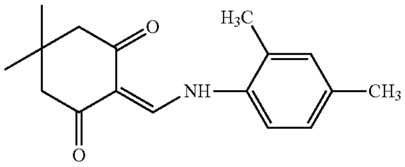

#10

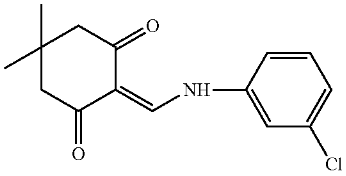

#11

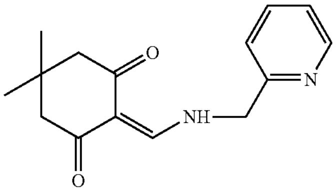

#12

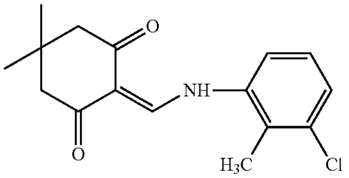

#13

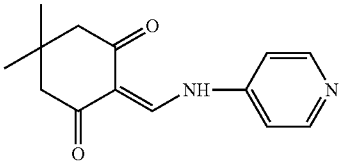

#14

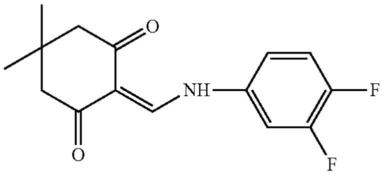

#15

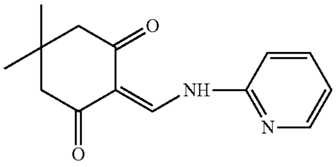

-continued
#16
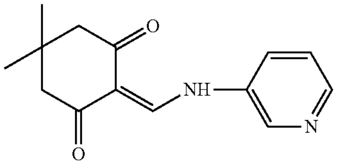
#17
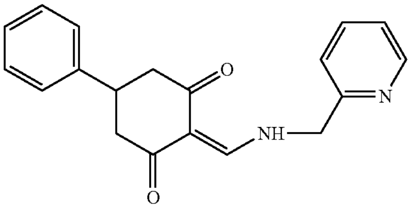
#19
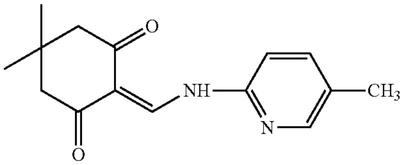
#20
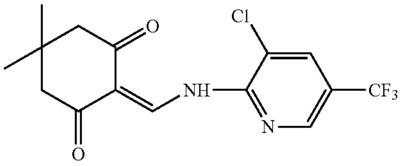
#22
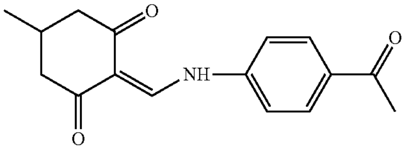
#23
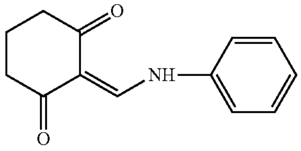
#24
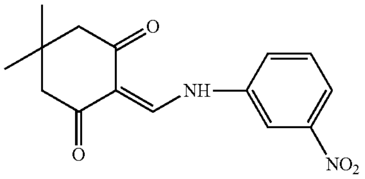
#25
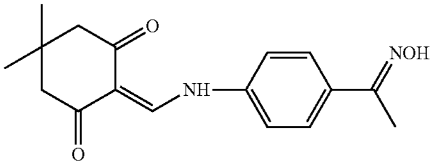
-continued
#26
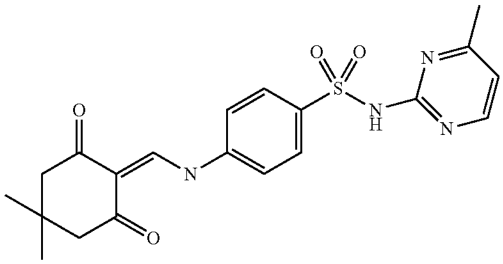
#27
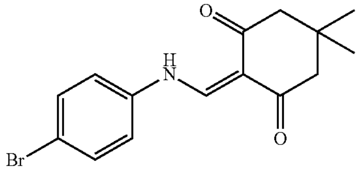
#28
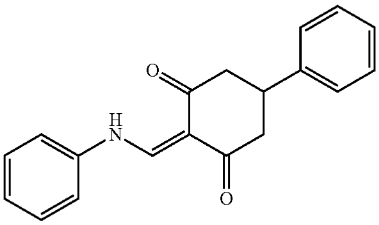
#29
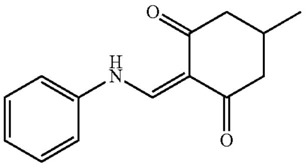
#30
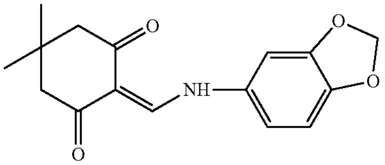
#31
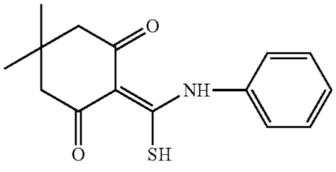
#32
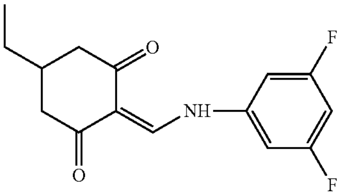
#33
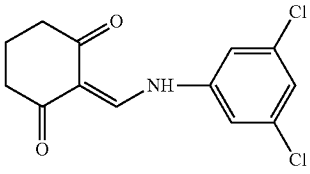

-continued
#34
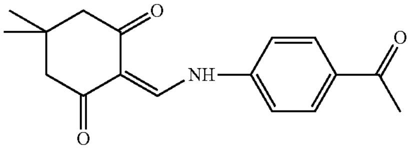
#35
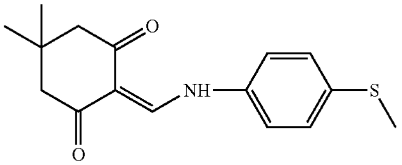
#36
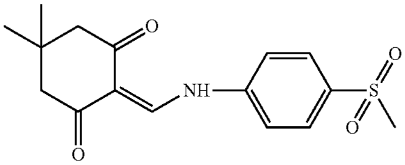
#37
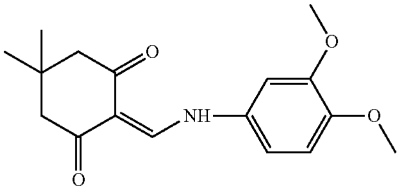
#38
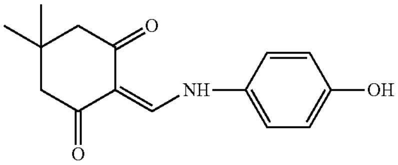
#39
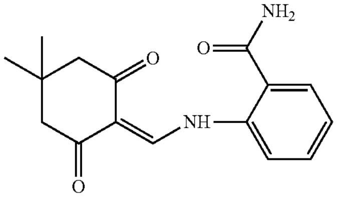
#40
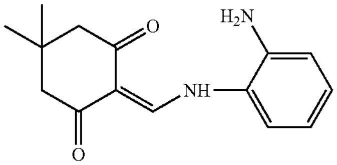
#41
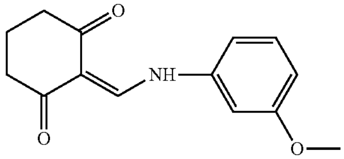
#42
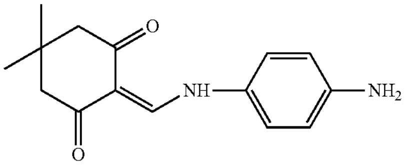
-continued
#43
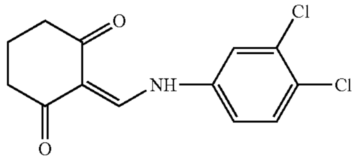
#44
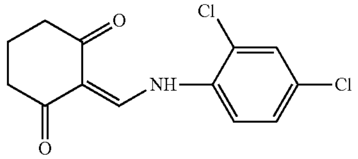
#45
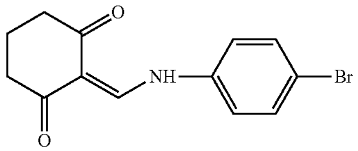 [SMILES: O=C1CCCC(=O)C1=CNc1ccc(Br)cc1]
#46
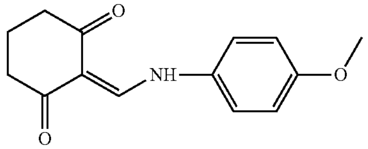 [SMILES: COc1ccc(NC=C2C(=O)CCCC2=O)cc1]
#47
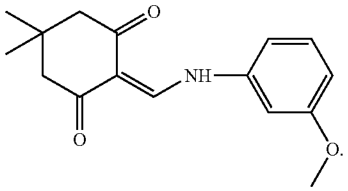
2. The method of claim 1, wherein the plant additive comprises at least one compound selected from the group consisting of MC2, #1-7, #9-16, #19-20, #22, #24-25, #27-28, #32-34, #36-39, #43-44 and #47 as set forth below:
MC2
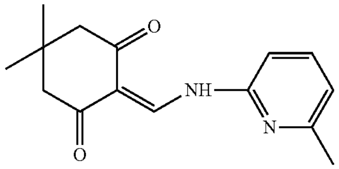
#1
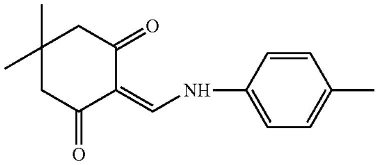
#2
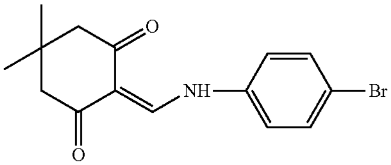

-continued
#3
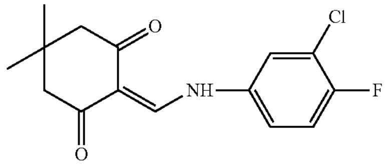
#4
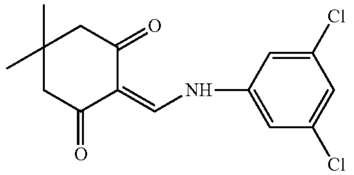
#5
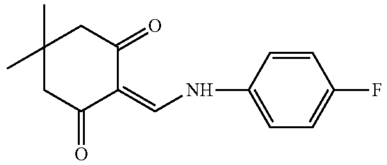
#6
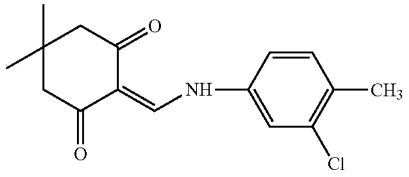
#7
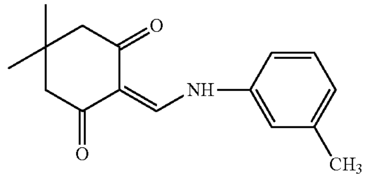
#9
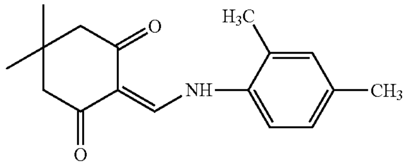
#10
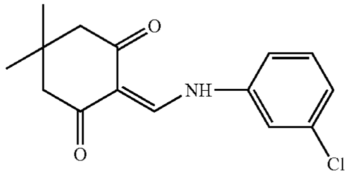
#11
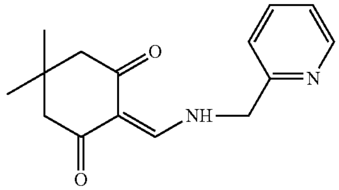
-continued
#12
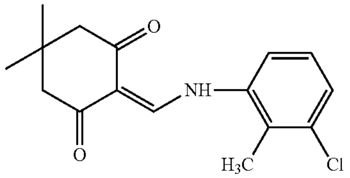
#13
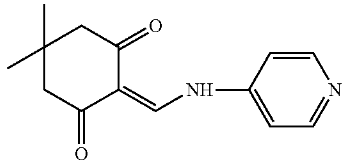
#14
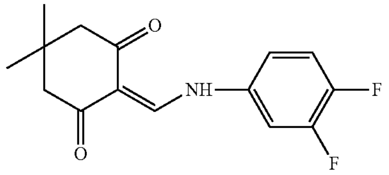
#15
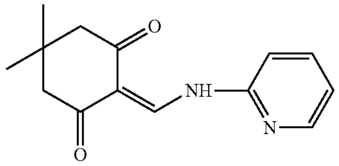
#16
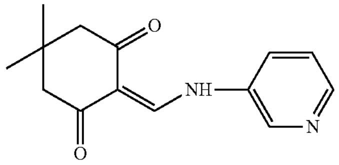
#19
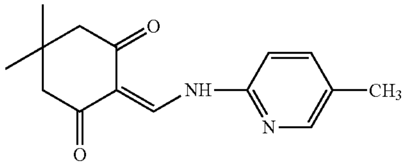
#20
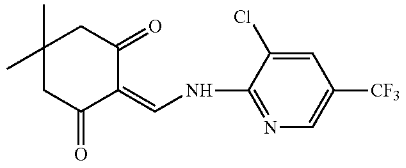
#22
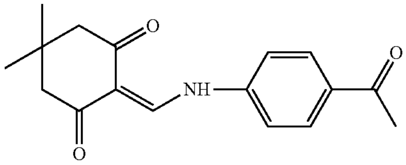
#24
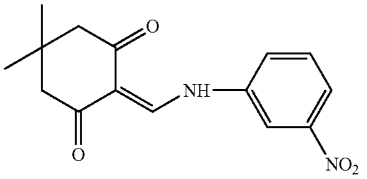

-continued

#25

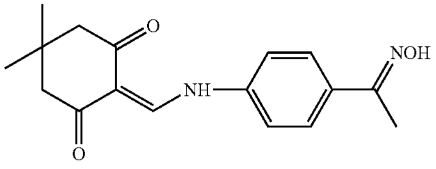

#27

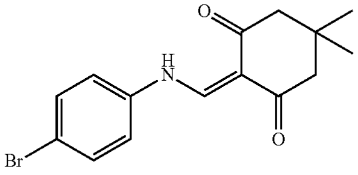

#28

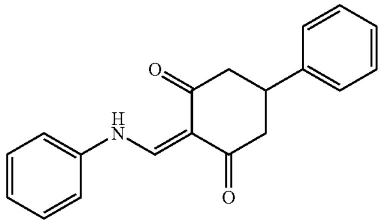

#32

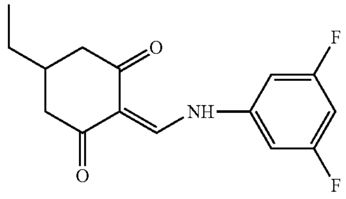

#33

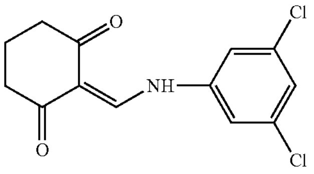

#34

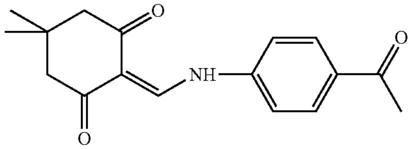

#36

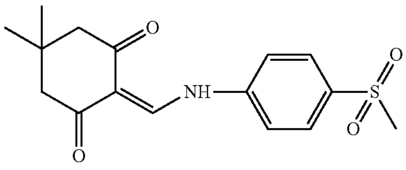

#37

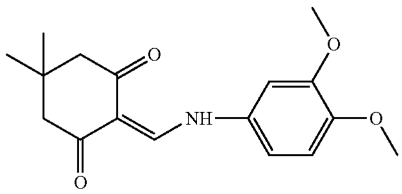

-continued

#38

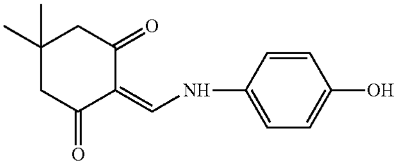

#39

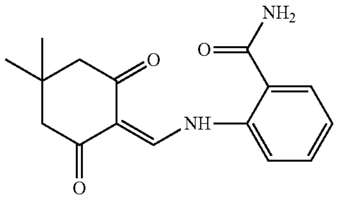

#43

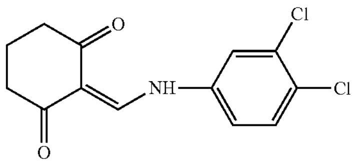

#44

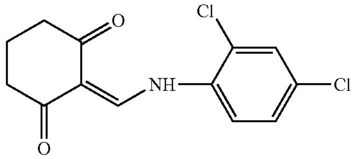

#47

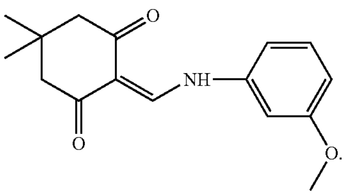

3. The method of claim 1, wherein the plant additive comprises at least one compound selected from the group consisting of #23, #29, #30, #31, #40, #41, #42, #45, and #46.

4. The method of claim 1, wherein the plant additive comprises at least one compound selected from the group consisting of #5, #20, #22, #27, #28, #37, #43, #44, and #47.

5. The method according to claim 1, wherein the plants are grown for biofuel production.

6. The method according to claim 1, wherein the plants are grown for plastid glycolipids production.

7. The method according to claim 1, wherein the plants require less phosphate fertilizer for growth.

* * * * *